US012303527B2

(12) United States Patent
Müller-Lierheim et al.

(10) Patent No.: US 12,303,527 B2
(45) Date of Patent: May 20, 2025

(54) HIGH MOLECULAR WEIGHT HYALURONIC ACID FOR TREATMENT AND PREVENTION OF SEVERE OCULAR SURFACE DISEASE

(71) Applicant: I.COM MEDICAL GMBH, Munich (DE)

(72) Inventors: Wolfgang Georg Konrad Müller-Lierheim, Munich (DE); Gysbert-Botho Van Setten, Danderyd (SE)

(73) Assignee: I.COM MEDICAL GMBH, Munich (DE)

( * ) Notice: Subject to any disclaimer, the term of this patent is extended or adjusted under 35 U.S.C. 154(b) by 0 days.

(21) Appl. No.: 17/048,451

(22) PCT Filed: Apr. 17, 2019

(86) PCT No.: PCT/EP2019/059965
§ 371 (c)(1),
(2) Date: Oct. 16, 2020

(87) PCT Pub. No.: WO2019/202017
PCT Pub. Date: Oct. 24, 2019

(65) Prior Publication Data
US 2021/0077523 A1    Mar. 18, 2021

Related U.S. Application Data

(60) Provisional application No. 62/659,215, filed on Apr. 18, 2018.

(51) Int. Cl.
*A61K 31/728* (2006.01)
*A61K 9/00* (2006.01)
*A61P 27/04* (2006.01)

(52) U.S. Cl.
CPC .......... *A61K 31/728* (2013.01); *A61K 9/0048* (2013.01); *A61P 27/04* (2018.01)

(58) Field of Classification Search
CPC ................ A61K 9/0048; A61K 31/728; A61P 27/00–04
USPC ........................................................... 514/54
See application file for complete search history.

(56) References Cited

U.S. PATENT DOCUMENTS

| | | | |
|---|---|---|---|
| 4,141,973 A | 2/1979 | Balazs | |
| 6,107,347 A | 8/2000 | Francese et al. | |
| 8,680,078 B2 | 3/2014 | Aleo et al. | |
| 8,853,150 B2 | 10/2014 | Barnes et al. | |
| 2005/0043271 A1 | 2/2005 | Gross et al. | |
| 2005/0164979 A1 | 7/2005 | Gross et al. | |
| 2009/0111770 A1 | 4/2009 | Holzer et al. | |
| 2012/0122976 A1 | 5/2012 | Holzer | |
| 2014/0221309 A1* | 8/2014 | Beard | A61K 47/12 514/57 |
| 2014/0228364 A1 | 8/2014 | Hadj-Slimane | |
| 2016/0193234 A1 | 7/2016 | Joo et al. | |
| 2017/0014339 A1* | 1/2017 | Mueller-Lierheim | A61K 31/728 |
| 2017/0071875 A1 | 3/2017 | Martinez et al. | |
| 2017/0071974 A1 | 3/2017 | Balazs et al. | |
| 2021/0145862 A1 | 5/2021 | Müller-Lierheim et al. | |
| 2021/0369764 A1 | 12/2021 | Müller-Lierheim et al. | |
| 2023/0233687 A1 | 7/2023 | Müller-Lierheim | |
| 2023/0241096 A1 | 8/2023 | Müller-Lierheim et al. | |
| 2023/0338541 A1 | 10/2023 | Müller-Lierheim | |

FOREIGN PATENT DOCUMENTS

| | | |
|---|---|---|
| CN | 104666139 A1 | 6/2015 |
| DE | 103 60 425 | 7/2005 |
| DE | 102005055275 A1 | 5/2007 |
| DE | 102009008940 A1 | 8/2010 |
| EP | 2070518 A2 | 6/2009 |
| EP | 2316420 A1 | 5/2011 |
| EP | 2543357 A1 | 1/2013 |
| EP | 3056195 A1 | 8/2016 |
| EP | 3525799 B1 | 1/2022 |
| JP | 2005-513106 A | 5/2005 |
| KR | 10-2009-0053892 A | 5/2009 |
| KR | 10-2012-0047851 A | 5/2012 |
| TW | 201945010 A | 12/2019 |
| WO | WO-94/09795 | 5/1994 |
| WO | WO 00/08061 A1 | 2/2000 |
| WO | WO-03/049747 | 6/2003 |
| WO | WO-03/053453 | 7/2003 |
| WO | WO-2008/072905 | 6/2008 |

(Continued)

OTHER PUBLICATIONS

Gregory, D. "New grading system and treatment guidelines . . ." Ophthalmology, vol. 123, No. 8, pp. 1653-1658. (Year: 2016).*
Ramappa, M. et al "Congenital corneal anesthesia" J. AAPOS, vol. 18, pp. 427-432. (Year: 2014).*
Messmer, E. "The pathophysiology and treatment of dry eye disease" Dtsch. Arzebl. Int., vol. 112, pp. 71-82. (Year: 2015).*
Downie, L. et al "A pragmatic approach to the management of dry eye disease . . ." Optom. Vis. Sci. vol 92, No. 9, pp. 1-10. (Year: 2015).*
Jain, R. et al "Stevens-Johnson syndrome: the role of the ophthamologist" Surv. Ophthalmol., vol. 61, pp. 369-399. (Year: 2016).*
Mueller-Lierheim, W. et al "Hyaluronic acid eye drops" Akt. Kontakt., pp. 1-3. (Year: 2015).*

(Continued)

*Primary Examiner* — Yih-Horng Shiao
(74) *Attorney, Agent, or Firm* — SALIWANCHIK, LLOYD & EISENSCHENK

(57) ABSTRACT

The invention concerns a method for reducing, preventing, or delaying the onset of severe ocular surface disease, or preventing or delaying the progression of mild or moderate ocular surface disease to severe ocular surface disease, by topically administering a fluid comprising high molecular weight hyaluronic acid to the ocular surface of the eye of a human or non-human animal subject, wherein the hyaluronic acid has an intrinsic viscosity of >2.5 m$^3$/kg and a concentration of <0.2% w/v.

11 Claims, No Drawings

(56) References Cited

FOREIGN PATENT DOCUMENTS

| WO | WO-2008/126803 | 10/2008 |
|---|---|---|
| WO | WO-2009/025763 | 2/2009 |
| WO | WO-2012/119261 | 3/2012 |
| WO | WO-2016/089807 | 6/2016 |
| WO | WO 2017/012712 | 1/2017 |
| WO | WO-2017/053339 | 3/2017 |
| WO | WO-2018/069763 | 4/2018 |
| WO | WO-2019/202015 | 10/2019 |
| WO | WO-2020/157570 | 8/2020 |
| WO | WO-2021/250462 | 12/2021 |
| WO | WO-2021/260427 | 12/2021 |
| WO | WO-2021/260430 | 12/2021 |

OTHER PUBLICATIONS

Das, S. et al "Recurrent corneal erosion syndrome" Surv. Ophthalmol., vol. 53, No. 1, pp. 3-15. (Year: 2008).*
Al-Assaf, S. et al. "Molecular interaction studies of the hyaluronan derivative, hylan A using atomic force microscopy" *Carbohydrate Polymers*, 2002, pp. 341-345, vol. 47.
Aragona, P. et al. "Modern approach to the treatment of dry eye, a complex multifactorial disease: a P.I.C.A.S.S.O. board review" Br J Ophthalmol, Apr. 2021 (Epub Jul. 2020), 105(4):446-453.
Ardizzoni, A. et al. "Influence of hyaluronic acid on bacterial and fungal species, including clinically relevant opportunistic pathogens" *J Mater Sci: Mater Med*, 2011, pp. 2329-2338, vol. 22.
Baenninger, P. B. et al. "Variability of Tear Osmolarity Measurements With a Point-of-Care System in Healthy Subjects-Systematic Review" *Cornea*, Jul. 2018, pp. 938-945, vol. 37, No. 7.
Balazs, E. A. and Leshchiner, E. A. "Hyaluronan, its cross-linked derivative—hylan—and their medical applications" *Cellulosics Utilization: Research and Rewards in Cellulosics, Proceedings of Nisshinbo International Conference on Cellulosics Utilization in the Near Future*, Elsevier Applied Science, NY, 1989, pp. 233-241.
Baudouin, C. "A new approach for better comprehension of diseases of the ocular surface" *J. Fr. Ophtalmol.*, 2007, 30(3):239-246; abstract.
Baudouin, C. et al. "Clinical impact of inflammation in dry eye disease: proceedings of the ODISSEY group meeting" *Acta Ophthalmologica*, 2017, pp. 1-9.
Baudouin, C. et al. "Diagnosing the severity of dry eye: a clear and practical algorithm" *Br J Ophthalmol*, 2014, pp. 1168-1176, vol. 98.
Beck, R. et al. "Hyaluronic Acid as an Alternative to Autologous Human Serum Eye Drops: Initial Clinical Results with High-Molecular-Weight Hyaluronic Acid Eye Drops" *Case Rep Ophthalmol*, 2019, pp. 244-255, vol. 10.
Belmonte, C. et al. "TFOS DEWS II pain and sensation report" *The Ocular Surface*, 2017, pp. 404-437, vol. 15, No. 3.
Benz, M. et al. "Lubrication and wear properties of grafted polyelectrolytes, hyaluronan and hylan, measured in the surface forces apparatus" *J. Biomed. Mater. Res.*, Oct. 2004, pp. 6-15, vol. 71A.
Berry, G.C. and Fox, T.G. "The Viscosity of Polymers and their Concentrated Solutions" *Adv. Polymer Sci.*, 1968, 5:261-357.
Bron, A. et al. "TFOS DEWS II pathophysiology report" *The Ocular Surface*, 2017, 15:438-510.
Caires, R. et al. "Hyaluronan modulates TRPV1 channel opening, reducing peripheral nociceptor activity and pain" *Nature Communications*, 2015, pp. 1-11, vol. 6, No. 8095.
Calciu-Rusu, D. et al. "Rheology of Sodium Hyaluronate Saline Solutions for Ophthalmic Use" *Biomacromolecules*, 2007, 8:1287-1292.
Camillieri, G. et al. "Hyaluronan-Induced Stimulation of Corneal Wound Healing is a Pure Pharmacological Effect" *J. Ocular Pharmacology & Therapeutics*, 2004, 20(6):548-553.
Cermelli, C. et al. "In vitro evaluation of antiviral and virucidal activity of a high molecular weight hyaluronic acid" *Virology Journal*, 2011, pp. 1-8, vol. 8, No. 141.

Code of Federal Regulations, Part 349—Ophthalmic Drug Products for Over-the-Counter Human Use, Nov. 14, 2019 (7 pages).
Comfort Shield® SD brochure. Copyright Nov. 2015; Manufacturer: i.com medical GmbH.
Condon, P. et al. "Double blind, randomised, placebo controlled, crossover, multicentre study to determine the efficacy of a 0.1% (w/v) sodium hyaluronate solution (Fermavisc) in the treatment of dry eye syndrome" *Br. J. Ophthalmol.*, 1999, 83:1121-1124.
Costagliola, C et al. "The ability of bacteria to use Na-hyaluronate as a nutrient" *Acta Ophthalmol. Scand.*, 1996, pp. 566-568, vol. 74.
Cowman, M. K. et al. "Tapping mode atomic force microscopy of the hyaluronan derivative, hylan A" *Carbohydrate Polymers*, 2000, pp. 229-235, vol. 41.
Craig, J. P. et al. "TFOS DEWS II Definition and Classification Report" The Ocular Surface, 2017, pp. 276-283, vol. 15, No. 3.
Cyphert, J. M. et al. "Size Matters: Molecular Weight Specificity of Hyaluronan Effects in Cell Biology" *International Journal of Cell Biology*, 2015, pp. 1-8.
Dick, H.B. et al. "Osmolality of various viscoelastic substances: Comparative study" *J. Cataract. Refract. Surg.*, 2000, 26:1242-1246.
Foulks, G.N. (Editor-in-Chief), "2007 Report of the International Dry Eye WorkShop (DEWS)" *The Ocular Surface*, Apr. 2007, vol. 5, No. 2 (142 pages).
Galor, A. et al. "Incomplete response to artificial tears is associated with features of neuropathic ocular pain" *Br. J. Ophthalmol.*, 2016, 100:745-749.
Gomis, A. et al. "Effects of Different Molecular Weight Elastoviscous Hyaluronan Solutions on Articular Nociceptive Afferents" *Arthritis & Rheumatism*, Jan. 2004, pp. 314-326, vol. 50, No. 1.
Gomis, A. et al. "Intra-articular injections of hyaluronan solutions of different elastoviscosity reduce nociceptive nerve activity in a model of osteoarthritic knee joint of the guinea pig" *Osteoarthritis and Cartilage*, 2009, pp. 798-804, vol. 17, No. 6.
Goyal, S. and Hamrah, P. "Understanding Neuropathic Corneal Pain-Gaps and Current Therapeutic Approaches" *Semin Ophthalmol.*, 2016, 31(1-2):59-70.
Graessley, W. "The Entanglement Concept in Polymer Rheology" *Adv. Polymer Sci.*, 1974, pp. 1-179.
Gross, D. et al. "Comparison of 0.2% and 0.18% hyaluronate eye drops in patients with moderate to severe dry eye with keratitis or keratoconjunctivitis" *Clinical Ophthalmology*, 2017, 11:631-638.
Higashide, T. et al. "Use of viscoelastic substance in ophthalmic surgery—focus on sodium hyaluronate" *Clinical Ophthalmology*, 2008, pp. 21-30, vol. 2, No. 1.
HYLAFORM® (hylan B gel) Explained, patient labeling, Jul. 28, 2004, 10 pages.
Hylan A-10, Material Safety Data Sheet, Genyzyme No. 7440-001, printed Mar. 16, 2005, pp. 1-6.
Jacobs, D. "Diagnosis and Treatment of Ocular Pain: the Ophthalmologist's Perspective" *Curr Ophthalmol Rep*, 2017, 5(4):271-275.
Japanese Pharmacopoeia JP XVII "Purified Sodium Hyaluronate Ophthalmic Solution" 2016, pp. 1577-1578.
Japanese Pharmacopoeia JP XVII "Purified Sodium Hyaluronate" 2016, pp. 1575-1576.
Jiang, D. et al. "Hyaluronan as an Immune Regulator in Human Diseases" *Physiol Rev*, 2011, 91:221-264.
Jones, L. et al. "TFOS DEWS II Management and Therapy Report" *The Ocular Surface*, 2017, pp. 575-628, vol. 15.
Kalluri, R. et al. "The basics of epithelial-mesenchymal transition" *The Journal of Clinical Investigation*, Jun. 2009, vol. 119, No. 6.
Kent, C. "Dry-Eye Guidelines: Making a Difference in the Clinic?" *Review of Ophthalmology*, Oct. 2008 (9 pages).
Knop, E. et al. "Anatomy and immunology of the ocular surface" *Chem Immunol Allergy*, 2007, pp. 36-49, vol. 92.
Koehler, L. et al. "Sulfated Hyaluronan Derivatives Modulate TGF-β1:Receptor Complex Formation: Possible Consequences for TGF-β1 Signaling" *Scientific Reports*, 2017, pp. 1-11, vol. 7, No. 1210.
Kojima, T. et al. "Autologous Serum Eye Drops for the Treatment of Dry Eye Diseases" *Cornea*, Sep. 2008, pp. S25-S30, vol. 27, No. 8, Suppl. 1.

(56) References Cited

OTHER PUBLICATIONS

Kojima, T. et al. "The Effects of High Molecular Weight Hyaluronic Acid Eye Drop Application in Environmental Dry Eye Stress Model Mice" *Int. J. Mol. Sci.*, 2020, pp. 1-15, vol. 21.

Krzoska, A. and Moest, P. "Effectiveness of Comfort Shield MDS—Results of a Clincal Investigation at Beuth Hochschule fur technik Berlin" *Galifa Augenblick*, Jul. 2016, pp. 1-8, in German, with English translation.

Kymionis, G. D. et al. "Treatment of chronic dry eye: focus on cyclosporine" *Clinical Ophthalmology*, 2008, pp. 829-836, vol. 2, No. 4.

Lee, D. G. et al. "Preventive Effects of Hyaluronic Acid on *Escherichia coli*-induced Urinary Tract Infection in Rat" *Urology*, 2010, vol. 75, No. 4.

Liu, X. et al. "Therapeutic Effects of Sodium Hyaluronate on Ocular Surface Damage Induced by Benzalkonium Chloride Preserved Anti-glaucoma Medications" Chin. Med. J., 2015, 128:2444-2449.

Löw, M et al. "Vergleich von Healon®, Healon® GV und Healon® 5 bei der Viskotrabekulektomie" *Ophthalmologe*, 2003, 100(7):539-544 (includes online machine translation). [LOW].

Lu, Q. et al. "An In Vitro Model for the Ocular Surface and Tear Film System" *Scientific Reports*, 2017, pp. 1-11, vol. 7, No. 6163.

Mazzacane, D. and Braggio, F. "Randomized controlled trial of high-molecular-weight hyaluronic acid in dry eye sindromes" *Ann. Di Oftalmo. e Clin. Oculist.*, 1993, 115:1-15.

Mehra, D. et al. "Ocular Surface Pain: A Narrative Review" *Ophthalmol Ther*, 2020, 9(3):1-21.

Messmer, E. M. "The Pathophysiology, Diagnosis, and Treatment of Dry Eye Disease" *Dtsch Arztebl Int*, 2015, pp. 71-82.

Mueller-Lierheim, W.G.K. "Guidelines. Tear substitute and contact rewetting solutions" *Aktkontaktol*, Apr. 2015, Issue 11, No. 24, pp. 8-15.

Mueller-Lierheim, W.G.K. "Why Chain Length of Hyaluronan in Eye Drops Matters" *Diagnostics*, 2020, 10:511 (32 pages).

Mueller-Lierheim, W.G.K. "New aspects of the use of hyaluronic acid on the ocular surface", presented at the annual meeting of the Romanian Contact Lens Society and Romanian Society of Cornea and Ocular Surface, Sibiu, Romania, Nov. 4-5, 2016, Poster and Abstract.

Mueller-Lierheim, W.G.K. "Tear substitutes. Latest information on hyaluronic acid" *Aktkontaktol*, Apr. 2015, Issue 11, No. 24, pp. 17-19.

Mueller-Lierheim, W.G.K. "The HYLAN M Study. Study design and first results" *Aktkontaktol*, Jan. 2017, Issue 13, No. 27 (3 pages).

Nakamura, M. et al. "Concentration and molecular weight dependency of rabbit corneal epithelial wound healing on hyaluronan" *Curr Eye Res*, 1992, 11(10):981-986.

Necas, J. et al. "Hyaluronic acid (hyaluronan): a review" *Veterinarni Medicina*, 2008, pp. 397-411, vol. 8.

Noble, P. W. "Hyaluronan and its catabolic products in tissue injury and repair" *Matrix Biol.*, Jan. 2002, pp. 25-29, vol. 21, No. 1.

Patel, S. et al. "Corneal Nerve Abnormalities in Ocular and Systemic Diseases" *Exp Eye Res*, 2021, 202:108284 (18 pages).

Pattmoeller, M. et al. "Safety of Hyaluronic Acid in Postoperative Treatment after Penetrating Keratoplasty" *Klin Monatsbl Augenheilkd*, 2018, 235:64-72.

Pavan, M. et al. "Hyaluronan derivatives: Alkyl chain length boosts viscoelastic behavior to depolymerization" *Carbohydrate Polymers*, 2013, pp. 321-326, vol. 97, No. 2.

Pena, E. et al. "TRPV1 channel modulation by hyaluronan reduces pain" *Channels*, 2016, pp. 81-82, vol. 10, No. 2.

Pflugfelder, S. C. et al. "Epithelial-Immune Cell Interaction in Dry Eye" *Cornea*, Sep. 2008, pp. 1-7.

Polack, F.M. and McNiece, M.T. "The Treatment of Dry Eyes with Na Hyaluronate (Healon®)" *Cornea*, Jun. 1982, pp. 133-136, vol. 1, No. 2.

Rah, M. J. "A review of hyaluronan and its ophthalmic applications" *Optometry*, 2011, pp. 38-43, vol. 82.

Rea, M. S. and Ouellette, M. J. "Relative visual performance. A basis for application" *Lightning Res. Technol.*, 1991, pp. 135-144, vol. 23, No. 3.

Salzillo, R. et al. "Optimization of hyaluronan-based eye drop formulations" *Carbohydrate Polymers*, 2016, pp. 275-283, vol. 153.

Schrager, H. M. et al. "Hyaluronic Acid Capsule and the Role of Streptococcal Entry into Keratinocytes in Invasive Skin Infection" Nov. 1996, pp. 1954-1958, vol. 98, No. 9.

Schultz, C. "Safety and Efficacy of Cyclosporine in the Treatment of Chronic Dry Eye" *Ophthalmology and Eye Diseases*, 2014, pp. 37-42, vol. 6.

Schulz, K. et al. "CONSORT 2010 Statement: Updated guidelines for reporting parallel group randomised trials" *J. Clin. Epidemiology*, 2010, pp. 1-7.

Shaheen, B. et al. "Corneal Nerves in Health and Disease" *Surv Ophthalmol.*, 2014, 59(3):263-285.

Shimmura, S. et al. "Sodium hyaluronate eyedrops in the treatment of dry eyes" *Br. J. Ophthalmology*, 1995, 79:1007-1011.

Shiseido, Certificate of Analysis, "Shiseido Sodium Hyaluronate SZE Grade •EP" Mar. 31, 2015.

Shiseido, Certificate of Suitability No. R1-CEP 2010-113-Rev 00, "Sodium Hyaluronate" Sep. 16, 2016.

Simsek, C. et al. "Alterations of Murine Subbasal Corneal Nerves After Environmental Dry Eye Stress" *IOVS*, Apr. 2018, pp. 1986-1995, No. 5, vol. 59.

Sodium hyaluronate, European Pharmacopoeia (Ph. Eur.) 9th Edition, Jan. 2017, pp. 3583-3585.

Stern, R. et al. "Hyaluronan fragments: An information-rich system" *European Journal of Cell Biology*, 2006, pp. 699-715, vol. 85.

Sullivan, B. D. et al. "An Objective Approach to Dry Eye Disease Severity" *Investigative Ophthalmology & Visual Science*, Dec. 2010, pp. 6125-6130, vol. 51, No. 12.

Sullivan, B.D. "Response to 'Variability of Tear Osmolarity Measurements With a Point-of-Care System in Healthy Subjects-Systematic Review'" *Cornea*, Jun. 2019, pp. e21-e23, vol. 38, No. 6.

Takigami, S. et al. "Hydration characteristics of the cross-linked hyaluronan derivative hylan" *Carbohydrate Polymers*, 1993, pp. 153-160, vol. 22.

Third party observation filed in related European Patent Application No. 17817868.7 on Dec. 11, 2020; in German with English translation.

Toda, I. et al. "Visual Performance After Reduced Blinking in Eyes With Soft Contact Lenses or After LASIK" *Journal of Refractive Surgery*, Jan. 2009, pp. 69-73, vol. 25.

Tsubota, K. et al. "A New Perspective on Dry Eye Classification: Proposal by the Asia Dry Eye Society" *Eye & Contact Lens*, 2020, 46(Supplement 1):S2-S13.

Tsubota, K. et al. "New Perspectives on Dry Eye Definition and Diagnosis: A Consensus Report by the Asia Dry Eye Society" *The Ocular Surface*, 2017, 15(1):65-76.

Van Setten et al. "High Molecular Weight Hyaluronan Promotes Corneal Nerve Growth in Severe Dry Eyes" *J. Clin. Med.*, 2020, 9:3799 (13 pages).

Van Setten, G. "Sandbank Epitheliopathy of the Conjunctiva (SEC) A New Indicator in Dry Eye Diagnostics Useful for Optimized Ocular Surgery" *Journal of Eye & Cataract Surgery*, 2017, pp. 1-4, vol. 3, No. 2:29.

Van Setten, G. "The Anatomical Dry Eye—A Different Form of Ocular Surface Disease Deserves Focus" *Open Journal of Ophthalmology*, Jul. 17, 2017, pp. 184-190, vol. 7.

Van Setten, G. B. "Osmokinetics: A new dynamic concept in dry eye disease" *Journal français d'ophtalmologie*, 2019, pp. 221-225, vol. 42.

Van Setten, G. et al. "Hyaluronic acid as an alternative to autologous human serum eye drops—initial clinical results with high molecular weight HA", Presented at the ESCRS Congress, Vienna, Switzerland, Sep. 16, 2018.

Van Setten, G-B. et al. "The HYLAN M Study: Efficacy of 0.15% High Molecular Weight Hyaluronan Fluid in the Treatment of Severe Dry Eye Disease in a Multicenter Randomized Trial" *J. Clin. Med.*, 2020, 9:3536 (25 pages).

(56) References Cited

OTHER PUBLICATIONS

White, C. et al. "Bringing comfort to the masses: A novel evaluation of comfort agent solution properties" *Contact Lens & Anterior Eye*, 2014, 37:81-91.
Wright, M. "Hylan Passes Initial Test for TX of Dry Eye" *Ophthalmology Times*, Oct. 1, 1993, p. 8.
Wu, C-L. et al. "Hyaluronic acid-dependent protection against alkali-burned human corneal cells" *Electrophoresis*, 2013, 34:388-396.
Duygu, G. et al. "The effects of high molecular weight hyaluronic acid (Hylan G-F 20) on experimentally induced temporomandibular joint osteoartrosis: part II" *Int. J. Oral Maxillofac. Surg.*, 2011, 40:1406-1413.
Mueller-Lierheim, W.G.K. "Hyaluronic acid eye drops. What you should know about their rheological properties" *Aktkontaktol*, Dec. 2015, Issue 11, No. 25, pp. 1-3.
Pistorius, A. et al. "The clinical application of hyaluronic acid in gingivitis therapy" *Quintessence Int.*, 2005, 36:531-538.
Romero-Jimenez, M. et al. "Keratoconus: A review" *Contact Lens Anter. Eye*, 2010, 33:157-166.
Anonymous, "A Brief Conversion Relationship Between Intrinsic Viscosity and Molecular Weight—Freshinechem", Jul. 5, 2018, pp. 1-2, Retrieved from the Internet: URL: https://www.freshinechem.com/a-brief-conversion-relationship-between-intrinsic-viscosity-and-molecular-weight/.
"ICD-10 Coding for Dry Eye", 2015, pp. 1-2.
Radda, T. M. et al. "Trockenes Auge—Therapie mit hypoosmolaren Natrium-Hyaluronat-Tropfen" *Spektrum der Augenheilkunde*, 1989, pp. 174-176, vol. 3/4 (includes machine translation).
U.S. Appl. No. 62/516,911, filed Jun. 8, 2017, pp. 1-42.
U.S. Appl. No. 62/408,559, filed Oct. 14, 2016, pp. 1-34.
Guidelines from BVA (Professional Association of Ophthalmologists) and DOG (German Ophthalmological Society) on dry eye (2019) (includes machine translation).
Schiffman et al. "Reliability and validity of the ocular surface index" *Arch Ophthalmology*, 2000, 118:615-621.
Miller et al. "Minimally Clinically Important Difference for the Ocular Surface Disease Index" *Arch Ophthalmology*, 2010, 128:94-101.
Ursapharm Product Catalogue from website, printed Feb. 2023.
Ocular Surface Disease Index (OSDI) questionnaire, 1995.
Leith et al. "Comparison of the properties of AMCISC® and Healon®" *Journal of Cataract & Refractive Surgery*, 1987, 13(5):534-6.
Hylo®-Gel Brochure—URSAPHARM.
Annotated Ursapharm viscosity chart including positions for Applicant products.
Aragona et al. "Physicochemical Properties of Hyaluronic Acid-Based Lubricant Eye Drops" *Translational vision science and technology*, 2019, 8(6): 1-11.
Notice of Opposition, dated Nov. 10, 2022, European Appl. No. 17817868.7.
Applicant response to opposition, dated Mar. 20, 2023, European Appl. No. 17817868.7.
Liao, Y-H. et al. "Hyaluronan: Pharmaceutical Characterization and Drug Delivery" *Drug Delivery*, 2005, 12:327-342.
Albano, G. et al. "Effect of High, Medium, and Low Molecular Weight Hyaluronan on Inflammation and Oxidative Stress in an In Vitro Model of Human Nasal Epithelial Cells" *Mediators of Inflammation*, 2016, pp. 1-13.
I.com medical, Munich, Facebook, Mar. 26, 2015, URL: www.facebook.com/icommedical.
Facebook, i.com medical, Mar. 26, 2015, URL: www.facebook.com/photo/?fbid=1556781561248541&set=pcb.1556781727915191.
Brief Communication, Opposition, dated Oct. 17, 2023, European Appl. No. 17817868.7.
Package insert of Hylo Fresh, Mar. 2021.
Package insert of Hylo Comod, Apr. 2022.
Package insert of Hylo Gel, Jun. 2022.
Davis, S. "Topical treatment options for allergic conjunctivitis" South African Family Practice, 2015, 57(4):10-15.
Akpek, E. et al. "A randomized trial of topical cyclosporin 0.05% in topical steroid-resistant atopic keratoconjunctivitis" Ophthalmology, 2004, 111:476-482.
Medic, N. et al. "Application frequency—key indicator for the efficiency of severe dry eye disease treatment—evidence for the importance of molecular weight of hyaluronan in lubricating agents" Acta Ophthalmologica, 2023, pp. 1-9.
Kaur, I. P. et al. "Penetration Enhancers and Ocular Bioadhesives: Two New Avenues for Ophthalmic Drug Delivery" Drug Development and Industrial Pharmacy, 2002, pp. 353-369, vol. 28, No. 4.
Higa, K. et al. "Therapeutic Aqueous Humor Concentrations of Latanoprost Attained in Rats by Administration in a Very-High-Molecular-Weight Hyaluronic Acid Eye Drop" Pharmaceutics, Apr. 9, 2024, pp. 1-10, vol. 16, No. 523.
Summons to attend oral proceedings pursuant to Rule 115(1) EPC in European Application No. 17817868.7 dated Oct. 24, 2023, pp. 1-31.
Brief Communication in European Application No. 17817868.7 dated Apr. 15, 2024, pp. 1-8.
New to combat dry eyes: Comfort Shield, Nov. 11, 2015, retrieved from Internet: https://www.optikum.at/ne-gegen-trocken-augen-comfort-shield/, in German with English translation, pp. 1-14.
Applicant response to summons, dated Apr. 11, 2024, European Appl. No. 17817868.7.
Wolffsohn, J. et al. "TFOS DEWS II Diagnostic Methodology Report" The Ocular Surface, 2017, pp. 539-574, vol. 15.
Dougherty, B. et al. "Rasch Analysis of the Ocular Surface Disease Index (OSDI)" Invest Ophthalmol Vis Sci., 2011, vol. 52, pp. 8630-8635.
Martin, R. "Comparison of the Ocular Surface Disease Index and the Symptom Assessment in Dry Eye Questionnaires for Dry Eye Symptom Assessment" Life, 2023, vol. 13, p. 1941 (13 pages).
Rahman, MQ et al. "The effect of pH, dilution, and temperature on the viscosity of ocular lubricants—shift in rheological parameters and potential clinical significance" Eye, 2012, pp. 1579-1584, vol. 26.
Bothner, H. et al. "Limiting viscosity No. and weight average molecular weight of hyaluronate samples produced by heat degradation" Int. J. Biol. Macromol., 1988, vol. 10, pp. 287-291.
Daull, P. et al. "Benefits of cetalkonium chloride cationic oil-in-water nanoemulsions for topical ophthalmic drug delivery" J. Pharm. Pharmacol., 2013, vol. 66, pp. 531-541.
Donnenfeld, E. et al. "Topical ophthalmic cyclosporine: pharmacology and clinical uses" Surv. Ophthalmol., 2009, vol. 54, No. 3, pp. 321-338.
Guter, M. et al. "Hyaluronan as a promising excipient for ocular drug delivery" Eur. J. Pharm. Biopharm., 2017, vol. 113, pp. 34-49.
Nepp, J. et al. "Arbeitsablauf zur Behandlung des Trockenen Auges, ein Versuch der Zuordnung von Diagnose zur Therapie" Spektrum Augenheilkd, 2016, vol. 30, pp. 122-136.
Written Submission in Preparation to/during Oral Proceedings in European Application No. 17817868.7 dated Jun. 10, 2024.
Decision revoking the patent; European Application No. 17817868.7 dated Jun. 25, 2024.
Grounds of Appeal; European Application No. 17817868.7 dated Oct. 21, 2024.

\* cited by examiner

HIGH MOLECULAR WEIGHT HYALURONIC ACID FOR TREATMENT AND PREVENTION OF SEVERE OCULAR SURFACE DISEASE

CROSS-REFERENCE TO RELATED APPLICATION

The present application is the National Stage of International Application Number PCT/EP2019/059965, filed Apr. 17, 2019, which claims the benefit of U.S. Provisional Application Ser. No. 62/659,215, filed Apr. 18, 2018, which is hereby incorporated by reference herein in its entirety, including any figures, tables, nucleic acid sequences, amino acid sequences, or drawings.

FIELD OF THE INVENTION

The present invention concerns a fluid for reducing or delaying the onset of severe ocular surface disease and/or after onset, its attenuation and long-term alleviation.

BACKGROUND OF THE INVENTION

According to the International Statistical Classification of Diseases and Related Health Problems 10th Revision, the scope of ocular surface disease (OSD) encompasses a variety of diseases. Some of them have links, or even causal relationships, to the insufficiency of the lacrimal apparatus. As evidenced by the ICD catalogue, however, the dry eye disease-associated OSDs are only a minor part in the total of all known severe diseases of the ocular surfaces. Nonetheless, diagnostic assessment with respect to the severity of ocular surface damage is very well established in the area of dry eye disease; consequently, some of these diagnostics may be utilized as an aid to identify the severity levels of other OSDs. Specifically, the ability to distinguish severe dry eye disease and more moderate degrees of intensity (Baudouin C et al., "Revisiting the Vicious Circle of Dry Eye Disease: a Focus on the Pathophysiology of Meibomian Gland Dysfunction", *Br J Ophthalmol*, 2016, 100(3):300-306), and the pattern of surface alteration (van Setten G, "Sandbank Epitheliopathy of the Conjunctiva (SEC): A New Indicator in Dry Eye Diagnostics Useful For Optimized Ocular Surgery, *J Eye Cataract Surg*, 2017, 3:1-4; and van Setten G, "The Anatomical Dry Eye—A Different Form of Ocular Surface Disease Deserves Focus", *Open Journal of Ophthalmology*, 2017, 7, 184-190), is very useful.

The goal of treatment of OSDs is the reversal of any pathology to the re-establishment of a normal situation, or as close to a normal situation as possible. In the optimal case of success this would be a complete recovery of disease and re-establishment of a condition exactly and as completely as it was before the onset of the disease, also called restitutio ad integrum (restoration to original condition). Disease is characterized by loss of any of the physiological features of the ocular surface, such as transparency, shape and form, elasticity, tectonic stability, etc., and the specific anatomical requirements to achieve and maintain these characteristics, such as innervations, epithelial integrity, extracellular matrix (ECM) composition, tissue hydration and dehydration, tissue structure, tissue surfaces, etc.

Severe ocular surface disease is a stage of disease in which the function of the ocular surface, or essential portions of it, such as transparency and tissue integrity, have become dysfunctional. The temporary or permanent character of the disease decides to which extent the mechanisms of associated pathology are reversible, if at all. The prevalence of a disease in a stage of higher severity, or the pathology associated with it, dictates whether there is an option of total reversibility or not. In cases of severe ocular surface disease, such as corneal scarring after trauma, the altered condition of the tissue itself may not allow a restitutio at integrum because the state of the tissue has permanently and irrevocably changed. If the severity of the ocular surface disease is characterized by a mere functional alteration, such as loss of transparency and surface hydration, and/or repairable surface damage, then full restoration, i.e., a complete recovery and healing, might be still possible. Thus, the extent of functional impairment correlates with the severity of the disease or the change of the condition. For example, the acute or chronic loss of transparency of the cornea due to severe corneal edema brought on by intraocular pressure or bare exposure to hypotonic conditions is a condition of severe ocular surface disease.

The invention is particularly directed to methods and compositions for use in treating severe ocular surface disease such as severe dry eye. As is understood by persons of skill in the art, severe dry eye is distinguishable from mild to moderate dry eye in etiology, symptoms and recommended treatments. The international Tear Film and Ocular Surface Society (TFOS) formed a group of subject matter experts, the Dry Eye WorkShop (DEWS), which formed subcommittees to address particular aspects of dry eye disease. One of these is the "Management and Therapy of Dry Eye Disease Subcommittee". The results of the discussions of the various subcommittees were submitted for publication in the form of two series of consensus papers, which represented the state of the art at the time of their publication in 2007 and 2017. These consensus papers included: A) "Management and Therapy of Dry Eye Disease: Report of the Management and Therapy Subcommittee of the International Dry Eye Work Shop (2007)", The Ocular Surface, April 2007, 5(2): 65-204 (referred to herein as "DEWS I (2007) report"; and B) "TFOS DEWS II Management and Therapy Report", The Ocular Surface, 2017, 15:575-628 (referred to herein as "DEWS II (2017) report".

The DEWS I (2007) report (at page 118) summarises the grading systems of ocular surface staining currently in use. The DEWS I (2007) report then defines in Table 2 (page 173) four dry eye severity levels, with Levels 1 and 2 corresponding to mild to moderate dry eye, and Levels 3 and 4 representing severe dry eye. Table 4 at page 174 shows a staged or stepped treatment approach in which recommended treatments are classified based on disease severity level. As shown in Table 4, there is a progression of treatment, tracking with the severity of the disease; thus, the "intensity" of the selected intervention is generally commensurate with the severity of dry eye. For example, artificial tear substitutes (which include hyaluronic acid eye drops) are considered suitable in the treatment of Level 1 disease, and anti-inflammatory agents are introduced for Level 2 disease, whereas Level 3 disease will likely call for autologous serum eye drops or other treatment commensurate with severe dry eye.

The DEWS II (2017) report echoes the expert consensus that "artificial tears" replace or supplement the natural tear film but do not target the underlying pathophysiology (see page 576, right column, Section 2.1). This consensus report states that there does not seem any substantial difference in effectiveness of artificial tear substitutes (see page 577, left column, section 2.1.1.1.1). Moreover, the expert opinion was that eye drops with high viscosity can increase retention time on the ocular surface, but may also cause transient visual disturbance and result in unwanted debris on the eyelids and lashes, leading to decreased tolerance and compliance. Very high viscosity eye drops are typically recommended for overnight use, with low-viscosity drops being used in the daytime. The DEWS II (2017) report describes the advantages of autologous serum over artificial tears for treating severe dry eye (see page 580, section 2.1.2.1).

Autologous serum eye drops are produced for the most severe stages of dry eye disease in patients where other eye drops failed or had to be discontinued. The beneficial effects of the substances included in serum drops have made them a valuable alternative for these patients. However, according to the state of the art, once such therapy has been introduced, it is virtually impossible to return to other lubricating eye drops. Further, there are disadvantages of using autologous serum eye drops for treatment of severe dry eye, such as the stringent regulatory requirements, and the cost and logistical burden of obtaining the patient's blood, and using a preservation method and storage system that prevents or minimizes degradation of important biological molecules such as growth factors and cytokines during storage and avoids contamination, which would lead to a risk of infection.

Therefore, there is a need for alternative means of treating severe dry eye that provide the required efficacy but do not have the drawbacks of the methods available in the art.

BRIEF SUMMARY OF THE INVENTION

The present invention provides a fluid composition for treating or preventing severe ocular surface disease (severe OSD). By topically administering a fluid composition containing a very high molecular weight form of hyaluronic acid (also called hyaluronan or HA) to the ocular surface, the invention can reduce severe ocular surface disease, prevent severe ocular surface disease, delay the onset of severe ocular surface disease, or prevent or delay further deterioration of the ocular surface by severe ocular surface disease.

Thus, in one preferred aspect the present invention provides a fluid for use in treating a severe ocular surface disease, wherein the fluid comprises high molecular weight hyaluronic acid having an intrinsic viscosity of >2.5 m$^3$/kg and a concentration of <0.2% w/v, wherein the severe ocular surface disease is severe dry eye, and wherein the fluid is for topical administration to the ocular surface of the eye of a human or non-human animal subject. It is particularly preferred that the hyaluronic acid has a molecular weight of at least 3 million Daltons, such as a molecular weight in the range of 3 million to 4 million Daltons. Further, it is preferred that the fluid comprises high molecular weight hyaluronic acid having a concentration of 0.1 to 0.19% w/v. Further, in a preferred embodiment the fluid may have: a) a pH of 6.8-7.6; b) an osmolarity of 240-330 mosmol/kg; c) a NaCl concentration of 7.6-10.5 g/l; and/or d) a phosphate concentration of 1.0-1.4 mmol/1. Yet further, it is preferred that the fluid is a clear and colourless solution, free from visible impurities and that the fluid is sterile. An example of a fluid for use according to the invention is Comfort Shield® preservative-free sodium hyaluronate eye drops.

DETAILED DESCRIPTION OF THE INVENTION

Hyaluronic acid (HA) is a carbohydrate—a mucopolysaccharide, specifically, which can be found in living organisms. The biological functions of endogenous HA include maintenance of the elastoviscosity of liquid connective tissues such as joint synovial fluid and eye vitreous fluid (Necas J et al., "Hyaluronic acid (hyaluronan): a review", *Veterinarni Medicina*, 2008, 53(8):397-411; Stern R et al., "Hyaluronan fragments: An information-rich system", *European Journal of Cell Biology*, 2006, 85:699-715). Although the specific mechanisms involved in the diverse signaling of HA are still poorly understood, it is known that HA can modulate multi-faceted biological effects that can vary depending on HA size (Cyphert J M et al., "Size Matters: Molecular Weight Specificity of Hyaluronan Effects in Cell Biology," *International Journal of Cell Biology*, 2015, Epub 2015 Sep. 10, 563818).

Sodium hyaluronate and other viscoelastic agents have been used in intraocular surgery since the 1970s and for treatment of dry eyes since the 1980s (Higashide T and K Sugiyama, "Use of viscoelastic substance in ophthalmic surgery—focus on sodium hyaluronate," Clinical Ophthalmology, 2008, 2(1):21-30; Polack F M and MT McNiece, "The treatment of dry eyes with Na hyaluronate (Healon)—preliminary report, 1982, 1(2):133-136); however, little attention has been paid thus far to the biological function of hyaluronic acid in epithelia (Müller-Lierheim WGK, "Tränenersatzlösungen, Neues über Hyaluronsäure," *Aktuelle Kontaktologie*, April 2015, 17-19).

An aspect of the invention includes a method for reducing, preventing, or delaying the onset of severe ocular surface disease, or preventing or delaying the transition of OSD from minor or moderate intensity to severe intensity, the method comprising topically administering a fluid comprising high molecular weight hyaluronic acid (HA) to the ocular surface of the eye of a human or non-human animal subject. The hyaluronic acid is high molecular weight, having an intrinsic viscosity of greater than 2.5 m$^3$/kg, and a concentration of <0.2% w/v. The intrinsic viscosity may be determined by the method of the European Pharmacopoeia 9.0, "Sodium Hyaluronate", page 3584 (which is incorporated herein by reference in its entirety). Briefly, the intrinsic viscosity [1] is calculated by linear least-squares regression analysis using the Martin equation: $\log_{10} (n_r-1/c)=\log_{10} [\eta]+\kappa[\eta]c$. In some embodiments, the hyaluronic acid has an intrinsic viscosity of greater than 2.9 m$^3$/kg.

In some embodiments, the hyaluronic acid has a concentration of 0.1 to 0.19% w/v.

In some embodiments, the fluid has: a) a pH of 6.8-7.6; b) an osmolarity of 240-330 mosmol/kg; c) a NaCl concentration of 7.6-10.5 g/l; and/or d) a phosphate concentration of 1.0-1.4 mmol/l.

In some embodiments the fluid is a clear and colourless solution, free from visible impurities. It is envisaged that the fluid is sterile.

In some embodiments the fluid according to the invention is Comfort Shield® preservative-free sodium hyaluronate eye drops.

In a preferred embodiment, the severe ocular surface disease is severe dry eye.

Another aspect of the invention includes a method for reducing the ease of, delaying, or preventing, the transition from temporary to permanent severe ocular surface disease, comprising topically administering a fluid comprising high molecular weight hyaluronic acid (HA) to the ocular surface of the eye of a human or non-human animal subject.

In some embodiments, the HA has a molecular weight of at least 3 million Daltons as calculated by the Mark-Houwink equation. In some embodiments, the HA has a molecular weight in the range of 3 million to 4 million Daltons as calculated by the Mark-Houwink equation.

In some embodiments, the high molecular weight HA is hyaluronan. In some embodiments, the high molecular weight HA is cross-linked, such as hylan A and hylan B. In some embodiments, the high molecular weight HA is non-cross-linked. In some embodiments, the high molecular weight HA is linear. In some embodiments, the high molecular weight HA is non-linear. In some embodiments, the high molecular weight HA is a derivative of hyaluronan, such as an ester derivative, amide derivative, or sulfated derivative, or a combination of two or more of the foregoing.

In some embodiments, the ocular surface to which the fluid is administered is in homeostasis at the time the fluid is administered. In other embodiments, the ocular surface of the eye of the subject is not in homeostasis.

The administered fluid can increase or enhance the visual performance of the eye to which it is administered, whether or not the ocular surface is in homeostasis at the time the fluid is administered to the eye. The administered fluid helps to stabilize the fluid film of the eye (e.g., the tear film at the ocular surface), optimizing vision and visual performance, especially under challenging conditions.

An increase or enhancement of visual performance can be defined as an increase or enhancement in the speed and/or accuracy of processing visual information. For example, visual performance can be described as how quickly and accurately an individual can process visual stimuli that are defined in terms of criteria such as adaptation luminance, target contrast, and target size. Methods for assessing visual performance and changes in visual performance are known in the art (see, for example, Toda I et al., "Visual performance after reduced blinking in eyes with soft contact lenses or after LASIK," *J Refract. Surg.*, 2009, January, 25(1):69-73; and Rea M S and MJ Quellette, "Relative visual performance: A basis for application," *Lighting Res. Technol.*, 1991, 23(3):135-144, which are incorporated herein by reference in their entirety).

The fluid may be administered to the ocular surface of one or both eyes of the subject by any topical administration method. For example, the fluid may be administered as one or more drops from a device for dispensing eye drops, such as an eye dropper. The fluid may be self-administered or administered by a third party. The dosage administered, as single or multiple doses, to an ocular surface will vary depending upon a variety of factors, including patient conditions and characteristics, extent of symptoms, concurrent treatments, frequency of treatment and the effect desired. For example, one or more drops (of, for example, about 30 microliters each) may be administered. While administration of 1-3 drops, one to three times per day, will be sufficient for mild to moderate ocular surface disease, more frequent topical administration may be needed for severe ocular surface disease, particularly during the initial phase of treatment, e.g., 1-3 drops for four, five, six, seven, eight, nine, ten, or more times per day.

Advantageously, in some embodiments, the frequency of administration and/or the amounts per dose can be decreased with time, as homeostasis of the ocular surface is preserved or restored and the cornea is stabilized. For example, in some cases, after four weeks, the amount administered may be reduced and/or the frequency of administrations each day may be reduced or the frequency of administrations may be reduced to semi-daily.

The fluid may be administered prophylactically, before the severe ocular surface disease exists, to reduce the severity of the severe ocular surface disease, prevent the severe ocular surface disease, and/or delay its onset; or the fluid may be administered therapeutically, after the severe ocular surface disease exists, to reduce the severity of the severe ocular surface disease. Optionally, the fluid is administered prophylactically before an event or stimulus occurs that causes the severe ocular surface disease, such as ocular trauma (e.g., non-surgical trauma), ocular surgery (e.g., glaucoma surgery, squint surgery, etc.), or infection of the eye. In some embodiments, onset of the severe ocular surface disease is delayed indefinitely (i.e., prevented). In some embodiments, one or more symptoms of the severe ocular surface disease are alleviated or eliminated. In some embodiments, all symptoms of the severe ocular surface disease are alleviated or eliminated.

The fluid may also be administered prophylactically to subjects that are particularly susceptible or prone to infection, in order to prevent or delay onset of severe ocular surface disease. For example, the subject may be immunocompromised. The subject's immunocompromised condition may have one or more causes, such as a medical treatment (e.g., radiation therapy, chemotherapy or other immunosuppressing treatment), environmental exposure (e.g., radiation exposure), or genetic defect, whether the defect is expressed as a phenotype, or not (i.e., as a genotype only). Subjects known to be immunocompromised, or having a genetic defect associated with being immunocompromised, even if not expressed as a phenotype, would benefit from prophylactic application of the invention, especially in anticipation of the subject being in challenging conditions for ocular surfaces.

In cases in which the severe ocular surface disease exists at the time of fluid administration and the fluid is administered therapeutically, optionally, the method further comprises the step of identifying the subject as having the severe ocular surface disease prior to administering the fluid.

In some embodiments, the severe ocular surface disease may have one or more of the following characteristics: leukocyte invasion at the ocular surface and tears, CD44 upregulation at the ocular surface, and activation of an immune cascade that includes one or more of IL-1, IL-2, IL-5, IL-6, IL-8, CXCL8, IL-10, IL-12, IL-16, IL-33, MCP1, CCL2, MIP1d (also known as CCL15), ENA-78, CXCL5, sILR1, sIL-6R, sgp sEGFR, sTNFR, I-17A, IL-21, IL-22, CXCL9, MIG, CXCL11, I-TAC, CXCL10, IP-10, MIP-13, CCL4, RANTES, and CCL5.

The severe ocular surface disease may be caused by various stimuli—external, internal, or both. In some embodiments, the severe ocular surface disease is caused by an external stimulus resulting in a disruption of the smoothness and/or integrity of the ocular surface (e.g., medical therapy, ocular surgery, non-surgical trauma, contact lens wearing, microbial infection, allergen, hapten, toxic agent, or irritative substance).

Various medical therapies, such as small molecule pharmaceuticals, and biologics, may cause the severe ocular surface disease. For example, the severe ocular surface disease may be caused by a "beta blocker", which refers to agents that inhibit or block the activity of one or more beta-adrenergic receptors. Beta blockers may be used for treatment of hypertension, stable and unstable angina, arrhythmias, migraine, bleeding esophageal varices, heart failure, and coronary artery disease, among other indications. Some beta-blockers antagonize one specific subtype of beta-adrenergic receptors (e.g., a beta-1 selective beta blocker which selectively antagonizes the beta-1 adrenergic receptor), whereas other beta-blockers are non-selective. Some beta-blockers can inhibit the effect of ligands such as noradrenaline or norepinephrine on one or more beta-adrenergic receptors. Accordingly, the term "beta-blocker" refers to all types of antagonists or inhibitors of beta-adrenergic receptors, regardless of whether the beta-blocker antagonizes one, two or more beta-adrenergic receptors and regardless of whether they affect other processes. Examples of beta-blockers include, but are not limited to, acebutolol, alprenolol, atenolol, betaxolol, bisoprolol, bopindolol, bucindolol, butaxamine, carteolol, carvedilol, celiprolol, esmolol, labetalol, levobunolol, medroxalol, metipranolol; metoprolol, nadolol, nebivolol, nadolol, oxprenolol, penbutolol, pindolol, propafenone, propranolol, sotalol, timolol, and eucommia bark.

In some embodiments, the severe ocular surface disease is allergy of the eye. In some embodiments, the severe ocular surface disease is non-infectious keratoconjunctivitis caused by an external damage, allergic keratoconjunctivitis (such as seasonal allergic keratoconjunctivitis), or infectious keratoconjunctivitis such as viral keratoconjunctivitis, bacterial conjunctivitis, fungal keratoconjunctivitis, and parasitic conjunctivitis. In some embodiments, the severe ocular surface disease is caused by an internal stimulus (e.g., hormonal disturbance (such as menopause and andropause), rheumatic disease, epithelial-mesenchymal transition (EMT), or autoimmune disorder).

The severe ocular surface disease may be caused by a wound of the eye. In some embodiments, the wound is caused by physical trauma, chemical trauma, or radiation (radiation injury). In some embodiments, the wound is caused by an ocular surgery. Examples of ocular surgeries include but are not limited to natural or artificial corneal transplantation, corneal implantation (e.g., intracorneal rings (ICRs), and keratoprosthesis), glaucoma surgery, cataract surgery (e.g., phacoemulsification, extracapsular cataract surgery, or intracapsular surgery), refractive surgery (e.g., radial keratotomy or refractive corneal incision), retinal surgery, squint (strabismus) surgery, corrective laser eye surgery (e.g., laser-assisted in situ keratomileusis (LASIK) or photorefractive keratectomy (PRK)), and cross-linking surgery. Administration of the fluid of the invention before, during, and/or after ocular surgery, such as glaucoma surgery, can improve clinical outcome, for example, by accelerating recovery, including recovery of visual performance after surgery, reducing scarring, and reducing itching, irritation, pain, and other discomfort.

The fluid may be administered to reduce or prevent or delay onset of ocular discomfort such as itchiness or ocular pain associated with severe ocular surface disease. The ocular pain may be associated with acute or chronic inflammation, or immune response. With the reduction of the pain, comes the reduction of secondary neuroinflammatory effects (Belmonte C et al., "TFOS DEWS II pain and sensation report", *The Ocular Surface*, 15:404-437). The cause of the pain may be known or unknown.

In some embodiments, the severe ocular surface disease is severe dry eye. In other embodiments, the severe ocular surface disease is a severe ocular surface disease other than severe dry eye.

In some embodiments, the severe ocular surface disease is one or more listed in the Table 1.

TABLE 1

| Examples of severe ocular surface disease | |
|---|---|
| Swelling of the cornea | Hayes, S. et al, "The structural response of the cornea to changes in stromal hydration", *J.R. Soc. Interface*, 2017, 14: 1-9. |
| Congenital corneal opacities | Mataftsi, A. et al., "Chromosome abnormalities and the genetics of congenital corneal opacification", *Molecular Vision*, 2011, 17: 1624-1640.<br>Nischal, K. K., "Genetics of Congenital Corneal Opacification-Impact on Diagnosis and Treatment," *Cornea*, 2015, 34 Suppl 10: S24-34. |
| Corneal scars | Rose J. S. et al., "Objective quantification of corneal haziness using anterior segment optical coherence tomography, *Journal of Current Ophthalmology*, 2018, 30(1): 54-57.<br>Torricelli, A. A. M. et al., "The corneal fibrosis response to epithelial-stromal injury," *Exp Eye Res.*, 2016, 142: 110-118. |
| Giant papillary conjunctivitis | Dunn, Jr., J. P. et al., "Giant papillary conjunctivitis associated with elevated corneal deposits, *Cornea*, 1990, (4): 357-8. |
| Cicatricial Pemphigoid | Ebrahimiadib, N. et al., "Atopy in Patients With Ocular Cicatricial Pemphigoid," *Cornea*, 2018, 37(4): 436-441. |
| Corneal haze with Impaired visual performance after laser treatment | Liu, Y. L. et al., "Visual performance after excimer laser photorefractive keratectomy for high myopia," *Taiwan J Ophthalmol*, 2017, 7(2): 82-88. |
| Severe ocular surface disease after Chemical burn | Javadi, M-A. et al., "Chronic and Delayed-Onset Mustard Gas Keratitis, Report of 48 Patients and Review of Literature, *Ophthalmology*, 2005, 112: (4): 1-11.<br>Baradaran-Rafii, A., "Mustard Gas Induced Ocular Surface Disorders", *Journal of Ophthalmic and Vision Research*, 2013, 8(4): 383-390. |
| Xerophthalmia | Rosen, D. S. et al., "Vitamin A deficiency and xerophthalmia in western Yemen," *Eur J Clin Nutr.*, 1996, 50(1): 54-7. |
| Trachoma with corneal scarring and vascularization | Whitcher, J. P., et al., "Corneal blindness: a global perspective", *Bull World Health Organ*, 2001, 79(3): 214-21. |
| Corneal scars after viral infections (measles) | Bowman, R. J. et al. "Non-trachomatous corneal opacities in the Gambia-aetiology and visual burden, *Eye* (Lond), 2002, 16(1): 27-32. |

In some embodiments, the severe ocular surface disease is one or more selected from among the following, as identified by TCD coding:

ICD-10-CM Codes>H00-H59 Diseases of the eye and adnexa>H15-H22
Disorders of sclera, cornea, iris and ciliary body>
Other disorders of cornea H18->
Codes
H00-H05 Disorders of eyelid, lacrimal system and orbit
H10-H11 Disorders of conjunctiva
H17.9 Corneal scars and opacifications, unspecified
H17.1 other central corneal opacifications
H17.8 specified corneal scars and opacifications
Corneal Haze with:
H15-H22 Disorders of sclera, cornea, iris and ciliary body
H53-H54 Visual disturbances and blindness
H55-H57 Other disorders of eye and adnexa
H59-H59 Intraoperative and post-procedural complications and disorders of eye and adnexa, not elsewhere classified.

Optionally, the fluid further includes one or more bioactive agents (e.g., a hydrophobic active ingredient). As used herein, the term "bioactive agent" refers to any substance that has an effect on the human or non-human animal subject when administered in an effective amount to affect the tissue. The bioactive agent may be any class of substance such as a drug molecule or biologic (e.g., polypeptide, carbohydrate, glycoprotein, immunoglobulin, nucleic acid), may be natural products or artificially produced, and may act by any mechanism such as pharmacological, immunological, or metabolic. Examples of classes of bioactive agents include substances that modify the pressure of the eye (e.g., enzyme inhibitors) and anti-angiogenic agents. Some specific examples of bioactive agents include steroids (e.g., corticosteroids), antibiotics, immunosuppressants, immunomodulatory agents, tacrolimus, plasmin activator, anti-plasmin, and cyclosporin A. In some embodiments, the bioactive agent is a steroid or antibiotic to treat or prevent eye infection; glaucoma drug such as prostaglandin analog, beta blocker, alpha agonist, or carbonic anhydrase inhibitor; agent for allergy eye relief such as histamine antagonist or non-steroidal anti-inflammatory drug; or mydriatic agent. Unfortunately, in some cases, the bioactive agent or agents included in the fluid may be irritative or damaging to the eye (e.g., cyclosporin A). Advantageously, through its rheological property and other properties, the high molecular weight HA in the fluid can alleviate and/or protect the eye from the irritative and/or damaging effects of the biologically active agent or agents within the fluid (i.e., the bioactive agent would be more irritative or more damaging to the eye if administered without the high molecular weight HA).

In some embodiments, the fluid contains no steroid, antibiotic or immunomodulator. In some embodiments, the fluid contains no other bioactive agent (e.g., no hydrophobic active ingredient).

In some circumstances, it may be desirable to include one or more preservatives or detergents within the fluid. Often, such preservatives and detergents are irritative or damaging to the eye. Advantageously, through its rheological property and other properties, the fluid can alleviate and/or protect the eye from the irritative and/or damaging effects of the preservative or detergent within the fluid. Thus, in some embodiments, the fluid further comprises a preservative or detergent that is irritative or damaging to the eye (i.e., a preservative or detergent that would be more irritative or more damaging to the eye if administered without the high molecular weight HA). In some embodiments, the fluid contains no preservative or detergent.

In some embodiments, the fluid includes cyclosporin A, cetalkoniumchloride, tyloxapol, or a combination of two or more of the foregoing.

In some embodiments, the fluid is administered to the subject before, during, and/or after administration of another composition comprising a bioactive agent to the subject. In some circumstances, it may be desirable to include one or more preservatives or detergents within the other composition. As indicated above, often, such preservatives and detergents are irritative or damaging to the eye, and some bioactive agents themselves may be irritative or damaging to the eye. Advantageously, through its rheological property and other properties, the fluid can alleviate and/or protect the eye from the irritative and/or damaging effects of the bioactive agent, preservative, and/or detergent within the other composition. Thus, the bioactive agent, preservative, and/or detergent within the other composition would be more irritative or more damaging to the eye if administered without the fluid.

In some embodiments, the other composition includes one or more of an antibiotic, immunosuppressant, or immunomodulatory agent.

In some embodiments, the other composition includes cyclosporin A, cetalkoniumchloride, tyloxapol, or a combination of two or more of the foregoing.

The other composition administered to the subject may be in any form and administered by any route (e.g., local or systemic). In some embodiments, the other composition is administered to the eye, e.g., topically or by injection. In some embodiments, the other composition is topically administered to the ocular surface.

In some embodiments, the preservative or detergent included in the fluid or other composition is a chemical preservative or oxidative preservative.

In some embodiments, the preservative or detergent included in the fluid or other composition is one that kills susceptible microbial cells by disrupting the lipid structure of the microbial cell membrane, thereby increasing microbial cell membrane permeability.

In some embodiments, the preservative or detergent included in the fluid or other composition is one that causes damage to the corneal tissues, such as corneal epithelium, endothelium, stroma, and interfaces such as membranes.

In some embodiments, the preservative or detergent included in the fluid or other composition is selected from the group consisting of quaternary ammonium preservative (e.g., benzalkonium chloride (BAK) or cetalkoniumchloride), chlorobutanol, edetate disodium (EDTA), polyquaternarium-1 (e.g., Polyquad™ preservative), stabilized oxidizing agent (e.g., stabilized oxychloro complex (e.g., Purite™ preservative)), ionic-buffered preservative (e.g., sofZia™ preservative), polyhexamethylene biguanide (PHMB), sodium perborate (e.g., GenAqua™ preservative), tyloxapol, and sorbate.

In some embodiments, the fluid is at least essentially mucin-free; or in other words having a mucin concentration of <0.3% w/v.

In some embodiments, the fluid includes a preservative. In other embodiments, the fluid does not include a preservative (i.e., the fluid is preservative-free).

In some embodiments, the fluid further includes a glycosaminoglycan (GAG), i.e., includes one or more GAGs in addition to the high molecular weight HA; electrolyte (e.g., sodium chloride); buffer (e.g., phosphate buffer); or a combination of two or more of the foregoing.

In some embodiments, the severe ocular surface disease is severe dry eye. In other embodiments, the severe ocular surface disease is a severe ocular surface disease other than severe dry eye.

The subject may or may not have dry eye syndrome (the aqueous tear deficiency type or qualitative dry eye type) at the time the fluid is administered to the eye of the subject. In some embodiments of the therapeutic or prophylactic methods, the eye of the subject to which the fluid is administered does not have aqueous tear deficiency (ATD) at the time of administering the fluid (i.e., in the absence of ATD). In some embodiments of the therapeutic or prophylactic methods, the eye of the subject to which the fluid is administered does not have qualitative dry eye at the time of administering the fluid (i.e., in the absence of qualitative dry eye). In some embodiments of the therapeutic or prophylactic methods, the eye of the subject to which the fluid is administered does not have dry eye syndrome at the time of administering the fluid (i.e., in the absence of aqueous tear deficiency or qualitative dry eye).

In some embodiments of the therapeutic or prophylactic methods, the subject is not suffering from a tear volume deficiency; however, the subject has an ocular surface abnormality (a topographic anomaly) comprising elevations on the cornea or elsewhere on the eye surface for which the normal tear film (tear film of normal surface tension and viscosity) does not cover, resulting in areas of friction at the ocular surface (van Setten, Epitheliopathy of the bleb (EoB)-identifying attrition: A new model for failure of glaucoma surgery, *New Frontiers in Ophthalmology,* 2018: 4(3): 1-4).

The fluid may be used in conjunction with a bandage contact lens. Thus, the method may further include applying a bandage contact lens to the eye before, during, and/or after administering the fluid. For example, the fluid may be administered before applying the bandage contact lens, after the contact lens, and/or placing fluid on the bandage contact lens before applying the bandage contact lens to the eye. Use of the fluid allows the bandage contact lens to exert pressure on the ocular surface while simultaneously minimizing friction at the ocular surface. Advantageously, the fluid and bandage contact lens can safely be used shortly after ocular surgery, e.g., glaucoma surgery.

Another aspect of the invention concerns a kit that may be used for carrying out the method of the invention described herein, i.e., reducing or delaying the onset of severe ocular surface disease. The kit comprises the fluid described herein, and one or more bandage contact lenses. Bandage contact lenses may be packaged together with the fluid within the same container (with the bandage contact lenses in contact with the fluid), or the bandage contact lenses may be separate from the fluid, packaged in separate containers. Suitable containers include, for example, bottles, vials, syringes, blister pack, etc. The containers may be formed from a variety of materials such as glass or plastic.

The kit may include a delivery agent (separately or in association with the fluid) that is to be brought into contact with the ocular surface or other part of the eye. For example, the kit may include particles (e.g., microparticles or nanoparticles) that are coated with the fluid and/or release the fluid onto the ocular surface.

Optionally, the kit may include a device for dispensing eye drops (e.g., an eye dropper), which may or may not serve as a container for the fluid in the kit before the kit's outer packaging is accessed (e.g., opened), i.e., the eye drop dispensing device may function to contain the fluid provided in the unaccessed (unopened) kit, or may be empty and receive the fluid after the kit is accessed. Optionally, the kit may include a label or packaging insert with printed or digital instructions for use of the kit, e.g., for carrying out the method of the invention.

Kits can include packaging material that is compartmentalized to receive one or more containers such as vials, tubes, and the like, each of the container(s) including one of the separate elements to be used in a method described herein. Packaging materials for use in packaging pharmaceutical products include, by way of example only U.S. Pat. Nos. 5,323,907, 5,052,558 and 5,033,252. Examples of pharmaceutical packaging materials include, but are not limited to, blister packs, bottles, tubes, pumps, bags, vials, light-tight sealed containers, syringes, bottles, and any packaging material suitable for a selected formulation and intended mode of administration and treatment.

A kit may include one or more additional containers, each with one or more of various materials desirable from a commercial and user standpoint for use of the compositions described herein. Non-limiting examples of such materials include, but not limited to, buffers, diluents, carrier, package, container, vial and/or tube labels listing contents and/or instructions for use, and package inserts with instructions for use.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In some embodiments of the kit, the fluid can be presented in a pack or dispenser device which can contain one or more unit dosage forms containing a composition disclosed herein. The pack can for example contain metal or plastic foil, such as a blister pack. The pack or dispenser device can be accompanied by instructions for administration.

Corneal Opacity

The severe OSD may be a corneal opacity. The fluid can enhance transparency (reduce opacity) partly or entirely, and prevent or delay onset of desiccation of the ocular surface. Advantageously, the fluid can avoid the need for a nurse to add water to the eye during an examination or procedure.

The corneal opacity may involve complete opacity or partial opacity, and may involve the entire ocular surface, or a portion of the ocular surface.

The corneal opacity may have one or more of a variety of causative or contributing agents. In some embodiments, the corneal opacity is caused by corneal edema, such edema caused by glaucoma; birth injury; or Fuchs dystrophy.

In some embodiments, the corneal opacity is caused by corneal scarring.

In some embodiments, the corneal opacity comprises a congenital corneal opacity. The congenital corneal opacity may be caused, for example, by birth trauma; Peters anomaly; dermoid tumor (limbal dermoid); sclerocornea; congenital hereditary endothelial dystrophy (CHED); mucopolysaccharidoses; congenital glaucoma, microphthalmia, metabolic disease infection; or inflammation.

In some embodiments, the corneal opacity is caused by a lack of blinking. For example, the lack of blinking may be due to a birth defect in a child that lacks the blinking reflex. In some embodiments, subject has Stevens-Johnson Syndrome.

In some embodiments, the corneal opacity is caused by inflammation; sensitivity to non-infectious bacteria; ulcer on the eye; infection; keratitis; trachoma; onchocerciasis (River blindness); dryness of the eye due to Sjogren syndrome, vitamin A deficiency, LASIK, LASEK, or PRK eye surgery; dystrophy (inherited metabolic disease); keratoconus; or injury to the eye (e.g., chemical burn, welding injury, etc.).

Optionally, the fluid may be administered in combination with another intervention for treatment of the corneal opacity or treatment of the cause of the opacity (e.g., antibiotic, steroid, phototherapeutic keratectomy (PTK), cornea transplant). The other intervention may be administered before, during or after administration of the fluid. If the other intervention involves administration of a bioactive agent, the bioactive agent may be included in the fluid or administered in a separate composition by a route suitable for the bioactive agent.

Acute and Chronic Ocular Surface Inflammation

Acute or chronic ocular surface inflammation may cause or contribute to a severe ocular surface disease. Ocular inflammation may take the form of numerous eye disorders of varying severity depending on the location of the inflammation. OSDs that may be attributed to ocular inflammation include, but are not limited to, uveitis, conjunctivitis, episcleritis, scleritis, optic neuritis, retrobulbar neuritis, keratitis, blepharitis, and the like. Many of these conditions can occur secondary to an infection of the eye, such as a bacterial, viral, fungal, or protozoan (e.g., amoeba) infection. Ocular inflammation can also result following ophthalmologic surgical procedures or ocular trauma resulting from physical injury of the eye.

Inflammation is a normal component of the immune response and a necessary component of the healing process, but is detrimental if it proceeds at an inappropriate level or duration. An acute leucocytic inflammation is triggered within hours of exposure to the causative agent (e.g., antigen, wound to the eye, or other insult) and represents a normal, time-limited inflammatory reaction. The end of this phase varies, but reduced inflammation provides an indirect sign of improvement and slow reconstitution to a prior state.

In contrast to acute ocular inflammation, chronic ocular inflammation is a state that is not merely different quantitatively in duration (i.e., prolonged), but also qualitatively different in kind. The differences between acute ocular inflammation and chronic ocular inflammation are significant, analogous to the differences between the immunological events in acute, healing wounds and chronic, non-healing wounds (see, for example, Tarnuzzer R W and Schultz G S, "Biochemical analysis of acute and chronic wound environments," *Wound Repair Regen.*, 1996, July-September, 4(3): 321-325). These differences in immunological events, particularly at conjunctival and subconjunctival tissue (as opposed to the cornea), underlie a diversity of ocular surface disorders and explain why some patients within a disease or disorder population are refractory to an otherwise effective treatment plan.

Ocular surface homeostasis is regulated by resident lymphocytes (CD8+ T cells, gamma delta T cells, and natural killer T cells) and CD4+ regulatory T cells, among other factors. These interact with anti-inflammatory factors, such as interleukin (IL)-1 receptor antagonist, transforming growth factor (TGF)-beta 2, and matrix protease inhibitors such as inhibitor of metalloproteinase (TIMP)-1. Stress factors including environment challenges, infections, endogenic stress, autoimmunity and genetic factors may all disturb the finely-tuned homeostatic balance existing on the ocular surface and activate an acute inflammatory response.

The method of the invention provides a holistic approach to establishing, restoring, and preserving ocular surface homeostasis, and thereby reduce or delay the onset of severe ocular surface disease. Thus, before or after onset, topical administration of the fluid can result in attenuation and long-term alleviation of the severe ocular surface disease.

Epithelial-derived pro-inflammatory cytokines activate immature resident antigen-presenting cells (APCs), which are mainly dendritic cells, on the ocular surface. Mature APCs migrate to the regional lymph nodes and initiate an adaptive immune response by priming naïve CD4+ T cells including T helper (Th)1 and Th17 cells. Through activated angiogenesis and lymphangiogesis, these inflammatory mediators traffic back to the ocular surface, where Th1-secreted interferon (IFN)-gamma and Th17-secreted IL-17 increased cytokine production, induce epithelial and goblet cell apoptosis and alter conjunctival homeostasis, perpetuating a chronic inflammatory process. In a state of goblet cell deficiency, the deprivation of gel-forming mucins leads to increased friction, thus perpetuating inflammation (Pflugfelder S C et al., "Epithelial-immune cell interaction in dry eye," *Cornea*, 2008, 27 Suppl 1:S9-11).

Whereas acute ocular surface inflammation is characterized by a rapid onset and relatively shorter duration (typically, a few minutes to a number of days), protein exudate, and the cellular infiltrate of the conjunctival and subconjunctival tissue is mainly neutrophils, chronic ocular surface inflammation is characterized by a longer duration (a number of days to years), fewer neutrophils, the cellular infiltrate is mainly macrophages and lymphocytes, and proliferation of blood vessels, fibrosis and tissue necrosis. Indeed, the primary cells of chronic ocular surface inflammation are macrophages and lymphocytes at the conjunctiva and subconjunctiva.

Typically, chronic ocular surface inflammation can also be identified by ocular surface inflammation markers including one or more of: tear film hyperosmolarity; elevated matrix metalloproteinase-9 (MMP-9) expression by epithelial cells and infiltrating leucocytes at the ocular surface; increased MMP-9 activity at the ocular surface (its MMP-3 and TIMP-1-mediated enzymatic activity); elevated interferon-gamma; over-expression of human leukocyte antigen-antigen D related (HLA-DR) by conjunctival epithelial cells; and intracellular adhesion molecule 1 (ICAM-1) by conjunctival epithelial cells, increased number of activated lymphocytes, and decreased number of goblet cells.

Steroids (e.g., corticosteroids) are considered the gold standard therapy for ocular inflammations. Dexamethasone, prednisolone, triamcinolone acetonide, fluocinolone acetonide and loteprednol etabonate are commonly employed, which act by various mechanisms such as inhibition of multiple inflammatory cytokines, fibrin deposition, polymorphonuclear leukocyte migration, and anti-angiogenesis effects by inhibition of nuclear factor-kappa-B (NF-kB) signal pathway (Nakao et al., *Am J Pathol.* 2007; 171(3): 1058-65).

The anti-inflammatory action of steroids is thought to be due to interference with arachidonic acid metabolism, i.e., by inhibition of phospholipase A2 which causes the release of arachidonic acid from the tissue phospholipid pool. Although steroids are effective in the treatment of ocular inflammation, their extended use is complicated by severe side effects, the most common of which are cataract formation, glaucoma, and infectious eye diseases (Kymionis G D et al., "Treatment of chronic dry eye: treatment of cyclosporine," *Clin Ophthalmol.* 2008 December; 2(4): 829-836; Schultz C, "Safety and efficacy of cyclosporine in the treatment of chronic dry eye," *Ophthalmol Eye Dis.* 2014; 6: 37-42). Likewise, immunomodulatory drugs such as cyclosporine and anti-inflammatory agents such as tetracycline and its derivatives can cause ocular pain and irritation in some patients (e.g., burning and itching), which can be difficult to tolerate in an inflamed eye.

Advantageously, topical administration of high molecular weight hyaluronic acid (HA), e.g., 3-4 MDa, may be used as an effective natural immunomodulator to regain ocular surface immune homeostasis in patient groups with chronic ocular surface inflammation or seasonal allergic keratoconjunctivitis, without the aforementioned agents or their side effects. In particular, fluids of the invention may be used to restore immune homeostasis of the ocular surface in these patients. Furthermore, other immunomodulatory agents may be administered to the subject before, during, or after administration of the high molecular weight HA, and the high molecular weight HA can make the environment at the ocular surface more conducive to the immunomodulatory agent's activity, enhancing or facilitating the action of the immunomodulatory agent.

The influence of the molecular weight of the HA molecules in eye drops on their bio-chemical function has very recently come into the focus of ophthalmic research. Due to its function in the extracellular matrix, HA plays an important role in the proliferation and differentiation of keratinocytes, in corneal wound healing, and in the homeostasis of the corneal epithelium. The prevalence of dry eyes in elderly persons is likely to be associated with the significant decrease of free HA in the extracellular matrix starting from the fifth decade. Moreover, HA acts as a signal molecule. Whereas, high molecular weight HA (3-4 MDa) acts anti-angiogenic and immunosuppressive, HA of medium molecular weight has inflammatory, immunostimulating, as well as angiogenic properties (Stern R et al., "Hyaluronan fragments: An information-rich system", *European Journal of Cell Biology,* 2006, 85:699-715; and Noble P W, "Hyaluronan and its catabolic products in tissue injury and repair," Matrix Biology, 2002, 21:25-29). Elevated enzyme levels in chronic inflammation cause increased hydrolysis of HA and thus a shift toward lower molecular weight. High molecular weight HA in eye drops can contribute to minimize this inflammation-related shift by decreasing friction at the ocular surface and supporting the down-regulation of the inflammatory process. A decrease of friction may also lead to a decrease of nociceptive neurological stimuli that can trigger the maintenance or onset of neurogenic inflammation supportive pathways.

It is well known that during acute and chronic inflammation various putative mediators of inflammation are released by the inflamed tissues and by leukocytes. The concentrations of these mediators and leukocytes are indicative of the level or degree of inflammation. Likewise, a reduction in concentration of these mediators and leukocytes is an indication of the effectiveness of a drug in treating inflammation. Examples of ocular surface inflammation markers include, but are not limited to, those listed above, i.e., tear film hyper-osmolarity; elevated matrix metalloproteinase-9 (MMP-9) expression by epithelial cells and infiltrating leucocytes at the ocular surface; increased MMP-9 activity at the ocular surface (its MMP-3 and TIMP-1-mediated enzymatic activity); elevated interferon-gamma; over-expression of human leukocyte antigen-antigen D related (HLA-DR) by conjunctival epithelial cells; and intracellular adhesion molecule 1 (ICAM-1) by conjunctival epithelial cells, increased number of activated lymphocytes, and decreased number of goblet cells.

Optionally, before administration of the fluid of the invention, the method of the invention may further comprise identifying the subject/eye as having chronic ocular surface inflammation by detecting or measuring one or more of these inflammatory markers of the ocular surface. Optionally, the method may further comprise detecting or measuring one or more of these inflammatory markers of the ocular surface one or more times after administration of the fluid of the invention in order to monitor the inflammatory status of the eye(s) over time and guide the frequency and duration of further administration of the fluid of the invention.

Fluid Preparation

As indicated above, the hyaluronic acid of the fluid has an intrinsic viscosity of greater than 2.5 m$^3$/kg and a concentration of <0.2% w/v. In some embodiments, the hyaluronic acid has an intrinsic viscosity of greater than 2.9 m$^3$/kg.

Viscoelasticity is defined as characteristics of a fluid having both viscous and elastic properties. The zero shear viscosity is determined as the steady shear plateau viscosity at vanishing shear rate. For highly viscous formulations, measurement with a controlled stress rheometer is preferred.

The relation between molecular weight and intrinsic viscosity [7] in m$^3$/kg is given through the Mark-Houwink equation:

$$[\eta] = k \cdot (M_{rm})a$$

with $M_{rm}$ being the molecular mass in MDa and the coefficients $$k = 1.3327 \cdot 10^{-4}$$

and $$a = 0.6691$$

which values for k and a having been found as most predictive.

The fluid may be produced by: sterilizing the filling line; adding purified water or water for injection (WFI) to a stainless steel mixing tank; adding salts while mixing; slowly adding HA and mixing until a homogeneous solution/fluid is achieved; adjusting pH value by adding NaOH or HCl, if required, while continuing the mixing process; transferring the solution over a 1 μm pore size filter cartridge to a sterile holding tank; and aseptically filling the solution via sterile filtration into the sterile primary package (monodose or vial). In the case of monodoses, this may be done by a blow-fill-seal (BFS) process.

Preferably, the fluid has at least essentially mucin-free or in other words having a mucin concentration of <0.3% w/v. This means that the flow behavior or properties essentially is reached or adjusted by hyaluronan and not by mucin naturally present in the subject's tear fluid and mainly responsible for the flow behavior thereof.

It is preferred that if substances are added that increase the viscosity, they are added towards, or during, or as a final step. The mixing is carried out so as to reach a homogeneous mixture. As an alternative or in addition, it is preferred to initially provide purified water or water for injection as a basis, and then, optionally, electrolytes, buffers and substances which do not increase the viscosity are added at first to the purified water or water for injection.

HA is further described in the monograph of the European Pharmacopoeia 9.0, page 3583 (Sodium Hyaluronate), which is incorporated herein by reference in its entirety.

In one embodiment, the fluid used in the method and kit of the invention has the characteristics listed in Table 2:

TABLE 2

| Characteristic | Specification | Test Method |
|---|---|---|
| Appearance | clear and colorless solution, free from visible impurities | Ph. Eur. |
| pH value | 6.8 - 7.6 | Ph. Eur. |
| Osmolality | 240 - 330 mosmol/kg | Ph. Eur. |
| HA concentration | 0.10 - 0.19% w/v | Ph. Eur. |
| NaCl concentration | 7.6 - 10.5 g/l | Ph. Eur. |
| Sterility | Sterile | Ph. Eur. |
| Phosphate concentration | 1.0 - 1.4 mmol/l | Ph. Eur. |

Exemplified Embodiments

Embodiment 1. A method for reducing or delaying the onset of severe ocular surface disease, comprising topically administering a fluid comprising high molecular weight hyaluronic acid to the ocular surface of the eye of a human or non-human animal subject, wherein the hyaluronic acid has an intrinsic viscosity of >2.5 m$^3$/kg and a concentration of <0.2% w/v.

Embodiment 2. The method of embodiment 1, wherein the fluid is administered prophylactically, before the severe ocular surface disease exists.

Embodiment 3. The method of embodiment 2, wherein the subject has a mild or moderate ocular surface disease at the time of administration, and the fluid is administered prophylactically to prevent or delay the progression of the ocular surface disease to a state of severe ocular surface disease.

Embodiment 4. The method of embodiment 1, wherein the fluid is administered therapeutically, after the severe ocular surface disease exists.

Embodiment 5. The method of any one of embodiments 1 to 4, wherein the severe ocular surface disease has one or more of the following characteristics: leukocyte invasion at the ocular surface and tears, CD44 upregulation at the ocular surface, and activation of an immune cascade that includes one or more of IL-1, IL-2, IL-5, IL-6, IL-8, CXCL8, IL-10, IL-12, IL-16, IL-33, MCP1, CCL2, MIP1d (also known as CCL15), ENA-78, CXCL5, sILR1, sIL-6R, sgp sEGFR, sTNFR, I-17A, IL-21, IL-22, CXCL9, MIG, CXCL11, I-TAC, CXCL10, IP-10, MIP-10, CCL4, RANTES, and CCL5.

Embodiment 6. The method of any preceding embodiment, wherein the severe ocular surface disease is caused by an external stimulus resulting in a disruption of the smoothness and/or integrity of the ocular surface (e.g., medical therapy, ocular surgery, non-surgical trauma, contact lens wearing, infection (e.g., bacterial, viral, or fungal), allergen, hapten, toxic agent, or irritative substance).

Embodiment 7. The method of any one of embodiments 1 to 5, wherein the severe ocular surface disease is caused by an internal stimulus (e.g., hormonal disturbance, rheumatic disease, epithelial-mesenchymal transition (EMT), or autoimmune disease).

Embodiment 8. The method of any preceding embodiment, wherein the severe ocular surface disease is caused by a wound of the eye.

Embodiment 9. The method of embodiment 8, wherein the wound is caused by physical trauma, chemical trauma, or radiation (radiation injury).

Embodiment 10. The method of embodiment 8, wherein the wound is caused by an ocular surgery.

Embodiment 11. The method of embodiment 10, wherein the ocular surgery is selected from among natural or artificial corneal transplantation, corneal implantation (e.g., intracorneal rings (ICRs), and keratoprosthesis), glaucoma surgery, cataract surgery (e.g., phacoemulsification, extracapsular cataract surgery, or intracapsular surgery), refractive surgery (e.g., radial keratotomy or refractive corneal incision), retinal surgery, squint (strabismus) surgery, corrective laser eye surgery (e.g., laser-assisted in situ keratomileusis (LASIK) or photorefractive keratectomy (PRK)), and cross-linking surgery.

Embodiment 12. The method of any preceding embodiment, wherein the severe ocular surface disease is accompanied by acute ocular surface inflammation.

Embodiment 13. The method of any one of embodiments 1 to 11, wherein the severe ocular surface disease is accompanied by chronic ocular surface inflammation.

Embodiment 14. The method of any one of embodiments 1 to 6, wherein the severe ocular surface disease is eye allergy.

Embodiment 15. The method of any one of embodiments 1 to 6, wherein the severe ocular surface disease is severe allergic keratoconjunctivitis (e.g., seasonal or non-seasonal) that causes one or more of the following in the subject: ocular pain; visual disturbance; acute loss of tissue homeostasis from a dysfunction of normal regulatory mechanism that maintain cellular hydration in tissues around the eye; and release of IgE and histamine.

Embodiment 16. The method of any preceding embodiment, wherein the severe ocular surface disease comprises a corneal opacity.

Embodiment 17. The method of embodiment 16, wherein the corneal opacity is caused by corneal edema.

Embodiment 18. The method of embodiment 17, wherein the corneal edema is caused by trauma; glaucoma; birth injury; or Fuchs dystrophy.

Embodiment 19. The method of embodiment 17, wherein the corneal opacity is caused by corneal scarring.

Embodiment 20. The method of embodiment 16, wherein the corneal opacity comprises a congenital corneal opacity.

Embodiment 21. The method of embodiment 16 or 20, wherein the corneal opacity is caused by birth trauma; Peters anomaly; dermoid tumor (limbal dermoid); sclerocornea; congenital hereditary endothelial dystrophy (CHED); mucopolysaccharidoses; congenital glaucoma, microphthalmia, metabolic disease infection; or inflammation.

Embodiment 22. The method of embodiment 16, wherein the corneal opacity is caused by a lack of blinking (e.g., due to a birth defect in a child without blink reflex).

Embodiment 23. The method of embodiment 16, wherein the subject has Stevens-Johnson Syndrome.

Embodiment 24. The method of embodiment 16, wherein the corneal opacity is caused by inflammation; sensitivity to non-infectious bacteria; ulcer on the eye; infection; keratitis; trachoma; onchocerciasis (River blindness); dryness of the eye due to Sjogren syndrome, vitamin A deficiency, LASIK, LASEK, or PRK eye surgery; dystrophy (inherited metabolic disease); keratoconus; or injury to the eye (e.g., chemical burn, welding injury, etc.).

Embodiment 25. The method of embodiment 16, wherein the fluid is administered in combination with another intervention for treatment of the corneal opacity or treatment of the cause of the opacity (e.g., antibiotic, steroid, phototherapeutic keratectomy (PTK), cornea transplant).

Embodiment 26. The method of any preceding embodiment, wherein the severe ocular surface disease causes discomfort such as itchiness or ocular pain.

Embodiment 27. The method of any preceding embodiment, wherein the subject is immunocompromised.

Embodiment 28. The method of any preceding embodiment, wherein the fluid contains no other bioactive agent (e.g., no hydrophobic active ingredient).

Embodiment 29. The method of any preceding embodiment, wherein the fluid contains no other immunomodulatory agent, immunosuppressive agent, or antibiotic.

Embodiment 30. The method of any one of embodiments 1 to 27, wherein the fluid further comprises a bioactive agent (e.g., a hydrophobic active ingredient).

Embodiment 31. The method of embodiment 30, wherein the bioactive agent is irritative or damaging to the eye.

Embodiment 32. The method of any one of embodiments 1 to 27, 29, 30, or 31 wherein the fluid further comprises a preservative or detergent.

Embodiment 33. The method of embodiment 32, wherein the preservative or detergent is irritative or damaging to the eye.

Embodiment 34. The method of any preceding embodiment, wherein the fluid is administered before, during, and/or after administration of a composition comprising: a bioactive agent (e.g., a hydrophobic active ingredient), preservative, detergent, or combination of two or more of the foregoing.

Embodiment 35. The method of embodiment 34, wherein the bioactive agent, preservative, detergent, or combination is irritative or damaging to the eye.

Embodiment 36. The method of any one of embodiments 32 to 35, wherein the preservative or detergent is a chemical preservative or oxidative preservative.

Embodiment 37. The method of any one of embodiments 32 to 36, wherein the preservative or detergent is one that kills susceptible microbial cells by disrupting the lipid structure of the microbial cell membrane, thereby increasing microbial cell membrane permeability.

Embodiment 38. The method of any one of embodiments 32 to 37, wherein the preservative or detergent is one that causes damage to the corneal tissues.

Embodiment 39. The method of any one of embodiments 32 to 38, wherein the preservative or detergent is selected from the group consisting of quaternary ammonium preservative (e.g., benzalkonium chloride (BAK)), chlorobutanol, edetate disodium (EDTA), polyquaternarium-1 (e.g., Polyquad™ preservative), stabilized oxidizing agent (e.g., stabilized oxychloro complex (e.g., Purite™ preservative)), ionic-buffered preservative (e.g., sofZia™ preservative), polyhexamethylene biguanide (PHMB), sodium perborate (e.g., GenAqua™ preservative), and sorbate.

Embodiment 40. The method of any preceding embodiment, wherein the fluid is administered directly to the ocular surface as drops or as a wash (e.g., lavage).

Embodiment 41. The method of embodiment 40, wherein 1 to 3 drops are administered, 1 to 3 times per day.

Embodiment 42. The method of any one of embodiments 1 to 40, wherein the severe ocular surface disease is accompanied by chronic ocular surface inflammation, and wherein 1 to 3 drops are administered, 4, 5, 6, 7, 8, 9, or 10 or more times per day.

Embodiment 43. The method of any one of embodiments 1 to 39, wherein the fluid is administered indirectly to the ocular surface by a delivery agent (a fluid delivery agent) that is topically administered to the ocular surface or other part of the eye (e.g., a particle that is coated with and/or secretes the fluid on to the ocular surface).

Embodiment 44. The method of any preceding embodiment, wherein the hyaluronic acid has an intrinsic viscosity of >2.9 m$^3$/kg.

Embodiment 45. The method of any one of embodiments 1 to 27, wherein the fluid further comprises a preservative.

Embodiment 46. The method of any one of embodiments 1 to 27, wherein the fluid does not further comprise a preservative (i.e., the fluid is preservative-free).

Embodiment 47. The method of any one of embodiments 1 to 27, wherein the fluid further comprises an additional glycosaminoglycan (GAG), an electrolyte (e.g., sodium chloride), a buffer (e.g., phosphate buffer), or a combination of two or more of the foregoing.

Embodiment 48. The method of any preceding embodiment, wherein the eye of the subject does not have aqueous tear deficiency (ATD) at the time of said administering (i.e., in the absence of ATD).

Embodiment 49. The method of any preceding embodiment, wherein the eye of the subject does not have qualitative dry eye at the time of said administering (i.e., in the absence of qualitative dry eye).

Embodiment 50. The method of any preceding embodiment, wherein the eye of the subject does not have dry eye syndrome at the time of said administering (i.e., in the absence of aqueous tear deficiency or qualitative dry eye).

Embodiment 51. The method of any preceding embodiment, wherein the subject is not suffering from an aqueous tear deficiency (ATD), and wherein the subject has an ocular surface abnormality (a topographic anomaly) comprising elevations on the cornea or elsewhere on the eye surface for which the normal tear film (tear film of normal surface tension and viscosity) does not cover, resulting in areas of friction at the ocular surface, and wherein the administered fluid reduces the friction.

Embodiment 52. The method of any preceding embodiment, wherein the eye of the subject is in homeostasis at the ocular surface at the time of said administering.

Embodiment 53. The method of any preceding embodiment, further comprising applying a bandage contact lens to the eye before, during, or after said administering.

Embodiment 54. The method of embodiment 53, wherein the fluid is administered and the bandage contact lens is applied after ocular surgery.

Embodiment 55. The method of any preceding embodiment, wherein the administered fluid increases visual performance of the eye.

Embodiment 56. The method of embodiment 54, wherein the fluid is administered before, during, and/or after ocular surgery, and wherein the subject recovers visual performance following the ocular surgery (i.e., recovers greater visual performance following the ocular surgery than the subject would have in the absence of administration of the fluid).

Embodiment 57. The method of any preceding embodiment, wherein the hyaluronic acid has a molecular weight of at least 3 million Daltons.

Embodiment 58. The method of any preceding embodiment, wherein the hyaluronic acid has a molecular weight in the range of 3 million to 4 million Daltons.

Embodiment 59. A kit comprising: the fluid of any one of embodiments 1 to 48, and one or more bandage contact lenses.

The present invention also concerns a fluid (a topical fluid) for topical administration to an ocular surface.

Embodiment 60. A fluid for use in reducing or delaying the onset of severe ocular surface disease, wherein the fluid comprises high molecular weight hyaluronic acid having an intrinsic viscosity of >2.5 m$^3$/kg and a concentration of <0.2% w/v, and wherein the fluid is topically administered to the ocular surface of the eye of a human or non-human animal subject.

Embodiment 61. The fluid of embodiment 60, wherein the fluid is administered prophylactically, before the severe ocular surface disease exists.

Embodiment 62. The fluid of embodiment 61, wherein the subject has a mild or moderate ocular surface disease at the time of administration, and the fluid is administered prophylactically to prevent or delay the progression of the ocular surface disease to a state of severe ocular surface disease.

Embodiment 63. The fluid of embodiment 60, wherein the fluid is administered therapeutically, after the severe ocular surface disease exists.

Embodiment 64. The fluid of any one of embodiments 60 to 63, wherein the severe ocular surface disease has one or more of the following characteristics: leukocyte invasion at the ocular surface and tears, CD44 upregulation at the ocular surface, and activation of an immune cascade that includes one or more of IL-1, IL-2, IL-5, IL-6, IL-8, CXCL8, IL-10, IL-12, IL-16, IL-33, MCP1, CCL2, MIP1d (also known as CCL15), ENA-78, CXCL5, sILR1, sIL-6R, sgp sEGFR, sTNFR, I-17A, IL-21, IL-22, CXCL9, MIG, CXCL11, I-TAC, CXCL10, IP-10, MIP-10, CCL4, RANTES, and CCL5.

Embodiment 65. The fluid of any one of embodiments 50 to 63, wherein the severe ocular surface disease is caused by an external stimulus resulting in a disruption of the smoothness and/or integrity of the ocular surface (e.g., medical therapy, ocular surgery, non-surgical trauma, contact lens wearing, microbial infection, allergen, hapten, toxic agent, or irritative substance).

Embodiment 66. The fluid of any one of embodiments 60 to 64, wherein the severe ocular surface disease is caused by an internal stimulus (e.g., hormonal disturbance, rheumatic disease, epithelial-mesenchymal transition (EMT), or autoimmune disease).

Embodiment 67. The fluid of any one of embodiments 60 to 65, wherein the severe ocular surface disease is caused by a wound of the eye.

Embodiment 68. The fluid of embodiment 67, wherein the wound is caused by physical trauma, chemical trauma, or radiation (radiation injury).

Embodiment 69. The fluid of embodiment 67, wherein the wound is caused by an ocular surgery.

Embodiment 70. The fluid of embodiment 69, wherein the ocular surgery is selected from among natural or artificial corneal transplantation, corneal implantation (e.g., intracorneal rings (ICRs), and keratoprosthesis), glaucoma surgery, cataract surgery (e.g., phacoemulsification, extracapsular cataract surgery, or intracapsular surgery), refractive surgery (e.g., radial keratotomy or refractive corneal incision), retinal surgery, squint (strabismus) surgery, corrective laser eye surgery (e.g., laser-assisted in situ keratomileusis (LASIK) or photorefractive keratectomy (PRK)), and crosslinking surgery.

Embodiment 71. The fluid of any one of embodiments 60 to 63, wherein the severe ocular surface disease is acute ocular surface inflammation.

Embodiment 72. The fluid of any one of embodiments 60 to 70, wherein the severe ocular surface disease is accompanied by chronic ocular surface inflammation.

Embodiment 73. The fluid of any one of embodiments 60 to 52, wherein the severe ocular surface disease is eye allergy.

Embodiment 74. The fluid of any one of embodiments 60 to 64, wherein the severe ocular surface disease is severe allergic keratoconjunctivitis (e.g., seasonal or non-seasonal) that causes one or more of the following in the subject: ocular pain; visual disturbance; acute loss of tissue homeostasis from a dysfunction of normal regulatory mechanism that maintain cellular hydration in tissues around the eye; and release of IgE and histamine.

Embodiment 75. The fluid of any one of embodiments 60 to 65, wherein the severe ocular surface disease causes discomfort such as itchiness or ocular pain.

Embodiment 76. The fluid of any one of embodiments 60 to 65, wherein the fluid is administered prophylactically, to prevent or delay the onset of the severe ocular surface disease, and wherein the subject is immunocompromised.

Embodiment 77. The fluid of any one of embodiments 60 to 66, wherein the fluid contains no other bioactive agent (e.g., no hydrophobic active ingredient).

Embodiment 78. The fluid of any one of embodiments 60 to 67, wherein the fluid contains no other immunomodulatory agent, immunosuppressive agent, or antibiotic.

Embodiments 79. The fluid of any one of embodiments 60 to 68, wherein the fluid further comprises a bioactive agent (e.g., a hydrophobic active ingredient).

Embodiment 80. The fluid of embodiment 79, wherein the bioactive agent is irritative or damaging to the eye.

Embodiment 81. The fluid of any one of embodiments 60 to 64, wherein the fluid further comprises a preservative or detergent.

Embodiment 82. The fluid of embodiment 81, wherein the preservative or detergent is irritative or damaging to the eye.

Embodiment 83. The fluid of any one of embodiments 60 to 64, wherein the fluid is administered before, during, and/or after administration of a composition comprising: a bioactive agent (e.g., a hydrophobic active ingredient), preservative, detergent, or combination of two or more of the foregoing.

Embodiment 84. The fluid of embodiment 83, wherein the bioactive agent, preservative, detergent, or combination is irritative or damaging to the eye.

Embodiment 85. The fluid of embodiment 81, wherein the preservative or detergent is a chemical preservative or oxidative preservative.

Embodiment 86. The fluid of embodiment 81, wherein the preservative or detergent is one that kills susceptible microbial cells by disrupting the lipid structure of the microbial cell membrane, thereby increasing microbial cell membrane permeability.

Embodiment 87. The fluid of embodiment 81, wherein the preservative or detergent is one that causes damage to the corneal tissues.

Embodiment 88. The fluid of embodiment 82, wherein the preservative or detergent is selected from the group consisting of quaternary ammonium preservative (e.g., benzalkonium chloride (BAK)), chlorobutanol, edetate disodium (EDTA), polyquaternarium-1 (e.g., Polyquad™ preservative), stabilized oxidizing agent (e.g., stabilized oxychloro complex (e.g., Purite™ preservative)), ionic-buffered preservative (e.g., sofZia™ preservative), polyhexamethylene biguanide (PHMB), sodium perborate (e.g., GenAqua™ preservative), and sorbate.

Embodiment 89. The fluid of any one of embodiments 60 to 63, wherein the fluid is administered directly to the ocular surface as drops or as a wash.

Embodiment 90. The fluid of embodiment 89, wherein 1 to 3 drops are administered, 1 to 3 times per day.

Embodiment 91. The fluid of any one of embodiments 60 to 63, wherein the inflammation is chronic ocular surface inflammation, and wherein 1 to 3 drops are administered 4, 5, 6, 7, 8, 9, or 10 or more times per day.

Embodiment 92. The fluid of any one of embodiments 60 to 63, wherein the fluid is administered indirectly to the ocular surface by a delivery agent that is topically administered to the ocular surface or other part of the eye (e.g., a particle that is coated with and/or secretes the fluid on to the ocular surface).

Embodiment 93. The fluid of any one of embodiments 60 to 63, wherein the hyaluronic acid has an intrinsic viscosity of >2.9 m$^3$/kg.

Embodiment 94. The fluid of any one of embodiments 60 to 63, wherein the fluid further comprises a preservative.

Embodiment 95. The fluid of any one of embodiments 60 to 63, wherein the fluid does not further comprise a preservative (i.e., the fluid is preservative-free).

Embodiment 96. The fluid of any one of embodiments 60 to 63, wherein the fluid further comprises an additional glycosaminoglycan (GAG), an electrolyte (e.g., sodium chloride), a buffer (e.g., phosphate buffer), or a combination of two or more of the foregoing.

Embodiment 97. The fluid of any one of embodiments 60 to 63, wherein the eye of the subject does not have aqueous tear deficiency (ATD) at the time of said administering (i.e., in the absence of ATD).

Embodiment 98. The fluid of any one of embodiments 60 to 63, wherein the eye of the subject does not have qualitative dry eye at the time of said administering (i.e., in the absence of qualitative dry eye).

Embodiment 99. The fluid of any one of embodiments 60 to 63, wherein the eye of the subject does not have dry eye syndrome at the time of said administering (i.e., in the absence of aqueous tear deficiency or qualitative dry eye).

Embodiment 100. The fluid of any one of embodiments 60 to 63, wherein the subject is not suffering from an aqueous tear deficiency (ATD), and wherein the subject has an ocular surface abnormality (a topographic anomaly) comprising elevations on the cornea or elsewhere on the eye surface for which the normal tear film (tear film of normal surface tension and viscosity) does not cover, resulting in areas of friction at the ocular surface, and wherein the administered fluid reduces the friction.

Embodiment 101. The fluid of any of embodiments 60 to 63, wherein the eye of the subject is in homeostasis at the ocular surface at the time of said administering.

Embodiment 102. The fluid of any one of embodiments 60 to 63, further comprising applying a bandage contact lens to the eye before, during, or after said administering.

Embodiment 103. The fluid of embodiment 102, wherein the fluid is administered and the bandage contact lens is applied after ocular surgery.

Embodiment 104. The fluid of any one of embodiments 60 to 63, wherein the administered fluid increases visual performance of the eye.

Embodiment 105. The fluid of embodiment 104, wherein the fluid is administered before, during, and/or after ocular surgery, and wherein the subject recovers visual performance following the ocular surgery.

Embodiment 106. The fluid of any one of embodiments 60 to 105, wherein the hyaluronic acid has a molecular weight of at least 3 million Daltons.

Embodiment 107. The fluid of any one of embodiments 60 to 106, wherein the hyaluronic acid has a molecular weight in the range of 3 million to 4 million Daltons.

Definitions

The term "a," "an," "the" and similar terms used in the context of the present invention (especially in the context of the claims) are to be construed to cover both the singular and plural unless otherwise indicated herein or clearly contradicted by the context. Thus, for example, reference "a cell" or "a compound" should be construed to cover both a singular cell or singular compound and a plurality of cells and a plurality of compounds unless indicated otherwise or clearly contradicted by the context. Similarly, the word "or" is intended to include "and" unless the context clearly indicates otherwise. The abbreviation, "e.g." is derived from the Latin exempli gratia, and is used herein to indicate a non-limiting example. Thus, the abbreviation "e.g." is synonymous with the term "for example."

The term "effective amount" in the context of the administered fluid of the invention means the amount of fluid necessary to obtain a desired result, such as reduction or elimination of the severe ocular surface disease, or reduction or elimination of a mild or moderate ocular surface disease and prevention or delayed progression to a severe ocular surface disease. In some embodiments, an effective amount may be the amount capable of preventing, delaying the onset of, treating, or ameliorating a severe ocular surface disease, or otherwise capable of producing an intended therapeutic effect.

The term "isolated," when used as a modifier of a composition, means that the compositions are made by human intervention or are separated from their naturally occurring in vivo environment. Generally, compositions so separated are substantially free of one or more materials with which they normally associate with in nature, for example, one or more protein, nucleic acid, lipid, carbohydrate, cell membrane. A "substantially pure" molecule can be combined with one or more other molecules. Thus, the term "substantially pure" does not exclude combinations of compositions. Substantial purity can be at least about 60% or more of the molecule by mass. Purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (for nucleic acid and peptide).

As used herein, the term "homeostasis" refers to the capacity of a physiological system to maintain internal stability, or to the state of stability itself, owing to the coordinated response of its parts to any situation or stimulus that would tend to disturb its normal, non-pathological condition or function.

As used herein, the term "hyaluronic acid" (HA) refers to the glycosaminoglycan composed of disaccharide repeats of N-acetylglucosamine and glucuronic acid found in nature, also known as hyaluronan (e.g., the straight chain, glycosaminoglycan polymer composed of repeating units of the disaccharide [-D-glucuronic acid-b1,3-N-acetyl-D-glucosamine-b1,4-]n), as well as derivatives of hyaluronan having chemical modifications such as esters of hyaluronan, amide derivatives, alkyl-amine derivatives, low molecular weight and high molecular weight forms of hyaluronans, and cross-linked forms such as hylans. Thus, the disaccharide chain may be linear or non-linear. Hyaluronan can be cross-linked by attaching cross-linkers such as thiols, methacrylates, hexadecylamides, and tyramines. Hyaluronan can also be cross-linked directly with formaldehyde and divinylsulfone. Examples of hylans include, but are not limited to, hylan A, hylan A (a formaldehyde cross-linked glycosaminoglycan polymer), hylan B (a divinylsulfone cross-linked glycosaminoglycan polymer), and hylan G-F 20 (Cowman M K et al., Carbohydrate Polymers 2000, 41:229-235; Takigami S et al., Carbohydrate Polymers, 1993, 22:153-160; Balazs E A et al., "Hyaluronan, its cross-linked derivative—Hylan—and their medical applications", in Cellulosics Utilization: Research and Rewards in Cellulosics, Proceedings of Nisshinbo International Conference on Cellulosics Utilization in the Near Future (Eds Inagaki, H and Phillips G O), Elsevier Applied Science (1989), NY, pp. 233-241; Koehler L et al., Scientific Reports, 2017, 7, article no. 1210; and Pavan M et al., Carbohydr Polym, 2013, 97(2): 321-326; which are each incorporated herein by reference in their entirety).

The term "hyaluronic acid" or HA includes HA itself and pharmaceutically acceptable salts thereof. The HA can be formulated into pharmaceutically-acceptable salt forms. Pharmaceutically-acceptable salts of HA can be prepared using conventional techniques.

The term "high molecular weight" or "HMW" in the context of hyaluronic acid of the invention refers to hyaluronic acid having an intrinsic viscosity of >2.5 $m^3/kg$ as determined by the method of the European Pharmacopoeia 9.0, "Sodium Hyaluronate", page 3584 (which is incorporated herein by reference in its entirety). Briefly, the intrinsic viscosity [η] is calculated by linear least-squares regression analysis using the Martin equation: $\text{Log}_{10} (n_r-1/c) = \log_{10} [\eta] + \kappa[\eta]c$. In some embodiments, the high molecular weight hyaluronic acid has an intrinsic viscosity of greater than 2.9 $m^3/kg$.

As used herein, the term "immunocompromised" refers to a subject with an innate, acquired, or induced inability to develop a normal immune response. An immunocompromised subject, therefore, has a weakened or impaired immune system relative to one of a normal subject. A subject with a weakened or impaired immune system has an "immunodeficiency" or "immunocompromised condition," which is associated with a primary or secondary deficiency, induced or non-induced, in one or more of the elements of the normal immune defense system. An immunocompromised condition may be due to a medical treatment, e.g., radiation therapy, chemotherapy or other immunosuppressing treatment, such as induced by treatment with steroids, cyclophosphamide, azathioprine, methotrexate, cyclosporine or rapamycin, in particular in relation to cancer treatment or the treatment or prevention of transplant rejection. The presence of an immunocompromised condition in a subject can be diagnosed by any suitable technique known to persons of skill the art. Strong indicators that an immunocompromised condition may be present is when rare diseases occur or the subject gets ill from organisms that do not normally cause diseases, especially if the subject gets repeatedly infected. Other possibilities are typically considered, such as recently acquired infections, for example, HIV, hepatitis, tuberculosis, etc. Generally, however, definitive diagnoses are based on laboratory tests that determine the exact nature of the immunocompromised condition. Most tests are performed on blood samples. Blood contains antibodies, lymphocytes, phagocytes, and complement components, all of the major immune components that might cause immunodeficiency. A blood cell count can be used to determine if the number of phagocytic cells or lymphocytes is below normal. Lower than normal counts of either of these two cell types correlates with an immunocompromised condition. The blood cells are also typically checked for their appearance. Sometimes, a subject may have normal cell counts, but the cells are structurally defective. If the lymphocyte cell count is low, further testing is usually conducted to determine whether any particular type of lymphocyte is lower than normal. A lymphocyte proliferation test may be conducted to determine if the lymphocytes can respond to stimuli. The failure to respond to stimulants correlates with an immunocompromised condition. Antibody levels and complement levels can also be determined for diagnosing the presence of an immunocompromised condition.

As used herein, the term "ocular surface" refers to the cornea and conjunctiva, and portions thereof, including the conjunctiva covering the upper and lower lids. The fluid may be topically administered to one or more parts of the ocular surface, including, for example, the entire ocular surface.

"Pharmaceutically acceptable salt" includes both acid and base addition salts. A pharmaceutically acceptable salt of HA or any one of the other compounds described herein is intended to encompass any and all pharmaceutically suitable salt forms. Preferred pharmaceutically acceptable salts described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra. In some embodiments, the pharmaceutically acceptable salt is sodium salt (see "Sodium Hyaluronate" at page 3583 of European Pharmacopoeia 9.0, which is incorporated herein by reference).

As used herein, the terms "subject", "patient", and "individual" refer to a human or non-human animal. A subject also refers to, for example, primates (e.g., humans), cows, sheep, goats, horses, dogs, cats, rabbits, rats, mice, fish, birds and the like. In some embodiments, the subject is a mammal. In some embodiments, the subject is a human. In some embodiments, the subject is a bird or fish. Thus, the methods may be carried out in the medical setting and the veterinary setting. The non-human animal subject may be, for example, a pet or an animal model of an ocular or non-ocular disease.

In some embodiments, the eye of the subject does not have aqueous tear deficiency (ATD) at the time of said administering (i.e., in the absence of ATD).

In some embodiments, the eye of the subject does not have qualitative dry eye at the time of said administering (i.e., in the absence of qualitative dry eye).

In some embodiments, the eye of the subject does not have dry eye syndrome at the time of said administering (i.e., in the absence of aqueous tear deficiency or qualitative dry eye).

In some embodiments, the subject is not suffering from an aqueous tear deficiency (ATD), and wherein the subject has an ocular surface abnormality (a topographic anomaly) comprising elevations on the cornea or elsewhere on the eye surface for which the normal tear film (tear film of normal surface tension and viscosity) does not cover, resulting in areas of friction at the ocular surface, and wherein the administered fluid reduces the friction.

In some embodiments, the subject is immunocompromised, i.e., is in an immunocompromised condition.

The phrase "topical administration" is used herein in its conventional sense to mean topical delivery to the desired anatomical site, such as the ocular surface. The fluid comprising high molecular weight hyaluronic acid may be applied directly or indirectly to the ocular surface by any manner that allows an effective amount of the fluid and ocular surface to make contact. For example, the fluid may be applied directly to the ocular surface, such as via eye drops or lavage, or applied indirectly via a delivery agent (i.e., a fluid delivery agent) that is brought into contact with the ocular surface or other part of the eye. An example of a delivery agent is a particle (e.g., microparticles or nanoparticles) that is coated with the fluid and/or releases the fluid onto the ocular surface. Such particles may be composed of various materials, such as natural or synthetic polymers. In some embodiments, the delivery agent may itself be administered as drops.

The invention is described only exemplarily by the embodiments in the description and drawings and is not limited thereto but rather includes all variations, modifications, substitutions, and combinations the expert may take from the complete documents of this application under consideration of and/or combination with his specific knowledge.

All patents, patent applications, provisional applications, and publications referred to or cited herein are incorporated by reference in their entirety, including all figures and tables, to the extent they are not inconsistent with the explicit teachings of this specification.

Following is an example that illustrates procedures for practicing the invention. These examples should not be construed as limiting. All percentages are by weight and all solvent mixture proportions are by volume unless otherwise noted.

Example 1-A Multi-Center, Multi-National Prospective Clinical Study on Patients with Severe Dry Eyes—the HYLAN M Study A multi-center, multi-national prospective, randomized clinical study on patients with severe dry eyes (according to the ODISSEY primary criteria) is being conducted in 12 study centers in 9 countries, referred to as the HYLAN M study. Within the study, the patients were randomized in two groups, one staying with the most effective individual patient treatment identified before, the other one switched to high molecular weight hyaluronic acid eye drops (Comfort Shield® preservative-free sodium hyaluronate eye drops (i.com medical GmbH, Munich, Germany)), which corresponds to the embodiment of Table 1 herein.

These patients (192 enrolled) have already received the best treatment their ophthalmologists could offer. All of the patients had been under "stable" therapy at the time of their inclusion into the study, i.e., their therapy has not been changed over a defined period of time prior to inclusion into this study. The patients are randomized into two groups, one group of patients remaining with their current therapy for dry eye syndrome, and the second group of patients treated with drops of the fluid described above (Comfort Shield® eye drops) in place of their tear substitute.

Study objectives included: (1) comparison of objective and subjective symptoms of dry eye under treatment with Comfort Shield® eye drops versus the tear substitute eye drops which the patients has been treated with before presenting to the investigator (=current therapy) in severe dry eye conditions; and (2) observation of objective performance, patients' subjective acceptance and adverse events of the eye drops. For each patient, both eyes were examined, and the eye with higher corneal fluorescein staining score at baseline examination was evaluated.

The patients in one of the study centers involved in the HYLAN M study had thus far not achieved adequate relief of signs and symptoms by all commercially available eye drops that the physicians had tested before deciding in favor of the treatment with autologous serum eye drops. They have included 11 patients with autologous serum eye drop treatment into the study. Out of these 11 patients, 6 have been randomized to the Comfort Shield® group, i.e. the use of autologous serum eye drops was replaced by Comfort Shield® over a period of 8 weeks. Out of these 6 patients, 2 discontinued their participation in the study, because Comfort Shield® eye drops did not provide adequate relief of symptoms. Two continued with the Comfort Shield® eye drop therapy over the eight weeks of the study, but preferred to return to their original therapy with autologous serum. The remaining two patients preferred Comfort Shield® eye drops over the autologous serum eye drops and decided to use the Comfort Shield® eye drops beyond the study.

Patients suffering from severe dry eye exhibit significant symptoms and usually have experienced a staged therapeutical treatment as outlined in the TFOS DEWS II Management and Therapy Report (see in particular FIG. 1 on page 608 and Table 16 on page 609). In the HYLAN M study only patients suffering from severe dry eye disease were included, who moreover were under stable treatment by the time of inclusion. As indicated above, the patients in this study were randomized in two groups, (a) the control group and (b) Comfort Shield® group. The control group continued with their therapy as by the time of inclusion, whereas, the Comfort Shield® group replaced the tear substitute used by the time of inclusion by Comfort Shield® eye drops. In this comprehensive, controlled clinical study, dry eye signs and symptoms are assessed at baseline, after 4 weeks and after 8 weeks. Dry eye symptoms were assessed by the use of the ocular surface disease index (OSDI), with OSDI score=33 or more as an inclusion criterium (Baudouin C et al., "Diagnosing the severity of dry eye: a clear and practical algorithm", *Br J Ophthalmol.*, 2014 September; 98(9):1168-76, which is incorporated herein by reference in its entirety).

Table 3 shows the development of symptoms over time at an interim statistical evaluation. After 8 weeks of treatment with Comfort Shield® eye drops, the OSDI score had improved by an average of 15.3 points, whereas the OSDI score of patients in the control group only improved by an average of 4.1 points. This result supports the conclusion that Comfort Shield® eye drops provide relief in the stage of severe dry eye where other tear substitutes fail to do so.

TABLE 3

|  | Control arm (N = 32) | Comfort Shield Arm (N = 29) | Total (N = 61) |
| --- | --- | --- | --- |
| WEEK 4 VISIT | 31 | 28 | 59 |
| Mean (Std) | −7.3 (13.2) | −12.1 (21.2) | −9.6 (17.5) |
| Median (IQR) | −6.6 (−13.3; 0.0) | −6.3 (−20.4; 0.9) | −6.3 (−16.7; 0.0) |
| [Min-Max] | — [−34.1-25.8] | — [−68.8-17.4] | [−68.8-25.8] |
| Missing data | 1 | 1 | 2 |
| WEEK 8 VISIT | 28 | 27 | 55 |
| Mean (Std) | −4.1 (16.0) | −15.3 (25.9) | −9.6 (22.0) |
| Median (IQR) | −3.2 (−13.5; 3.8) | −12.5 (−30.0; 1.7) | −5.3 (−18.8; 2.3) |
| [Min-Max] | — [−43.0-40.9] | — [−84.1-27.1] | [−84.1-40.9] |
| Missing data | 4 | 2 | 6 |

Data provided by Coronis, GmbH, sponsor of the study.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method of treating severe ocular surface disease comprising:
   a) measuring the ocular surface disease index (OSDI) of a human subject or a non-human subject and selecting a human subject or non-human animal subject having severe ocular surface disease, on the basis of an OSDI score of at least 33, for treatment with a fluid;
   b) topically administering the fluid, said fluid comprising high molecular weight hyaluronic acid (HMWHA) to the ocular surface of the eye of the selected human subject or non-human animal subject having severe ocular surface disease, wherein the hyaluronic acid has an intrinsic viscosity of >2.5 m$^3$/kg and a concentration of <0.2% w/v to reduce severe dry eye symptoms and wherein the severe ocular surface disease is: a) severe dry eye; b) caused by an external stimulus resulting in a disruption of the smoothness and/or integrity of the ocular surface;
   or c) caused by an internal stimulus.

2. The method of claim 1, wherein the severe ocular surface disease is severe dry eye.

3. The method of claim 1, wherein the severe ocular surface disease is caused by an external stimulus resulting in a disruption of the smoothness and/or integrity of the ocular surface.

4. The method of claim 1, wherein the severe ocular surface disease is caused by an internal stimulus.

5. The method of claim 1, wherein the hyaluronic acid has an intrinsic viscosity of >2.9 m$^3$/kg.

6. The method of claim 1, wherein the hyaluronic acid has a molecular weight of at least 3 million Daltons.

7. The method according to claim 1, wherein the fluid has a pH between 6.8 and 7.6, and has an osmolality between 240 and 330 mosmol/kg, comprises between 0.10 and 0.19% w/v HMWHA, a sodium chloride at a concentration between 7.6 and 10.5 g/l, and a phosphate at a concentration between 1.0 and 1.4 mmol/l, and is sterile.

8. The method according to claim 1, wherein the fluid reduces severe dry eye symptoms as measured by the ocular surface disease index (OSDI).

9. The method according to claim 1, wherein the method improves OSDI scores for the selected human subject or non-human animal subject having severe ocular surface disease treated with said fluid.

10. The method according to claim 1, wherein the fluid does not contain another bioactive agent used for treating severe ocular surface disease.

11. The method according to claim 2, wherein the fluid does not contain another bioactive agent used for treating severe ocular surface disease.

* * * * *